United States Patent
Kawagishi et al.

(10) Patent No.: US 9,241,689 B2
(45) Date of Patent: Jan. 26, 2016

(54) ULTRASONIC DIAGNOSTIC EQUIPMENT AND IMAGING PROCESSING APPARATUS

(75) Inventors: Tetsuya Kawagishi, Kuroiso (JP); Naohisa Kamiyama, Otawara (JP)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 597 days.

(21) Appl. No.: 10/933,248

(22) Filed: Sep. 3, 2004

(65) Prior Publication Data

US 2005/0101863 A1 May 12, 2005

(30) Foreign Application Priority Data

Sep. 5, 2003 (JP) ................................. 2003-314718

(51) Int. Cl.
*A61B 8/06* (2006.01)
*A61B 8/08* (2006.01)
*A61B 8/13* (2006.01)
*A61B 8/00* (2006.01)

(52) U.S. Cl.
CPC . *A61B 8/481* (2013.01); *A61B 8/06* (2013.01); *A61B 8/13* (2013.01); *A61B 8/543* (2013.01)

(58) Field of Classification Search
CPC ............ A61B 8/06; A61B 8/13; A61B 8/481; A61B 8/543
USPC ................. 600/465, 458, 437, 440, 443, 447; 73/596–602, 618–633, 640–644; 345/619, 629–635, 639, 640; 382/107, 382/128, 130, 131, 133, 134, 276, 282, 284, 382/286, 287, 298, 299
See application file for complete search history.

(56) References Cited

U.S. PATENT DOCUMENTS

| | | | | |
|---|---|---|---|---|
| 4,932,415 A | * | 6/1990 | Angelsen et al. | 600/455 |
| 5,107,838 A | * | 4/1992 | Yamaguchi | 600/410 |
| 5,156,152 A | * | 10/1992 | Yamazaki et al. | 600/454 |
| 5,241,473 A | * | 8/1993 | Ishihara et al. | 600/443 |
| 5,285,788 A | * | 2/1994 | Arenson et al. | 600/441 |
| 5,359,513 A | * | 10/1994 | Kano et al. | 382/128 |
| 5,456,255 A | * | 10/1995 | Abe et al. | 600/443 |

(Continued)

FOREIGN PATENT DOCUMENTS

| | | |
|---|---|---|
| JP | 11-155858 | 6/1999 |
| JP | 11-155862 | 6/1999 |

(Continued)

*Primary Examiner* — Mark Remaly
(74) *Attorney, Agent, or Firm* — Oblon, McClelland, Maier & Neustadt, L.L.P.

(57) ABSTRACT

Each of an ultrasonic diagnostic equipment and an image processing apparatus according to the present invention comprises image acquisition device configured to acquire image data by scanning a patient into whom an ultrasonic contrast medium has been injected, with ultrasonic beams, same-part correspondence device configured to bring same parts into correspondence with each other, between a plurality of images concerning the same parts of the identical patient and acquired by the image acquisition device, arithmetic operation device configured to arithmetically operate image information items on changes of intensities between the plurality of images by using the intensities of those corresponding pixels of the plurality of images which have been brought into correspondence by the pixel correspondence device, and display device configured to display results operated by the arithmetic operation device.

36 Claims, 16 Drawing Sheets

(56) References Cited

U.S. PATENT DOCUMENTS

| | | | |
|---|---|---|---|
| 5,465,721 A * | 11/1995 | Kishimoto et al. | 600/443 |
| 5,485,561 A * | 1/1996 | Iizuka et al. | 382/282 |
| 5,615,680 A * | 4/1997 | Sano | 600/437 |
| 5,694,937 A * | 12/1997 | Kamiyama | 600/443 |
| 5,795,296 A * | 8/1998 | Pathak et al. | 600/443 |
| 5,958,881 A * | 9/1999 | Korman | 424/9.1 |
| 6,004,270 A * | 12/1999 | Urbano et al. | 600/443 |
| 6,071,494 A * | 6/2000 | Unger | 424/9.4 |
| 6,080,107 A * | 6/2000 | Poland | 600/458 |
| 6,123,670 A * | 9/2000 | Mo | 600/447 |
| 6,193,660 B1 * | 2/2001 | Jackson et al. | 600/443 |
| 6,201,543 B1 * | 3/2001 | O'Donnell et al. | 345/420 |
| 6,290,648 B1 * | 9/2001 | Kamiyama | 600/443 |
| 6,413,217 B1 * | 7/2002 | Mo | 600/440 |
| 6,436,049 B1 * | 8/2002 | Kamiyama et al. | 600/458 |
| 6,447,454 B1 * | 9/2002 | Chenal et al. | 600/449 |
| 6,643,537 B1 * | 11/2003 | Zatezalo et al. | 600/432 |
| 6,803,910 B2 * | 10/2004 | Pfister et al. | 345/420 |
| 6,811,766 B1 * | 11/2004 | Eriksen et al. | 424/9.52 |
| 6,839,456 B2 * | 1/2005 | Touzawa et al. | 382/128 |
| 6,884,407 B1 * | 4/2005 | Unger | 424/9.52 |
| 2002/0165454 A1 * | 11/2002 | Ogasawara et al. | 600/443 |
| 2004/0077952 A1 * | 4/2004 | Rafter et al. | 600/481 |

FOREIGN PATENT DOCUMENTS

| | | | |
|---|---|---|---|
| JP | 3023290 | 1/2000 | |
| JP | 2002209898 A * | 7/2002 | A61B 8/06 |
| JP | 2003-164452 | 6/2003 | |
| WO | WO 99/49899 | 10/1999 | |
| WO | WO 9949899 A2 * | 10/1999 | A61K 49/00 |

* cited by examiner

BEFORE STRESSING

AFTER STRESSING

EXAMPLE OF OPERATED RESULT

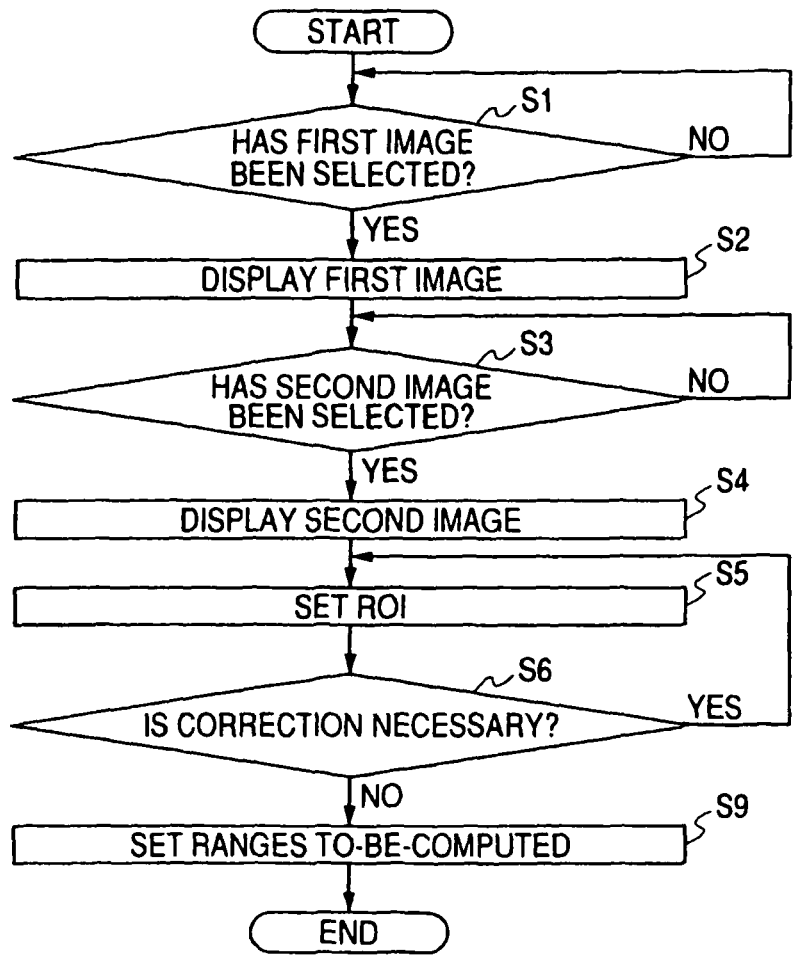
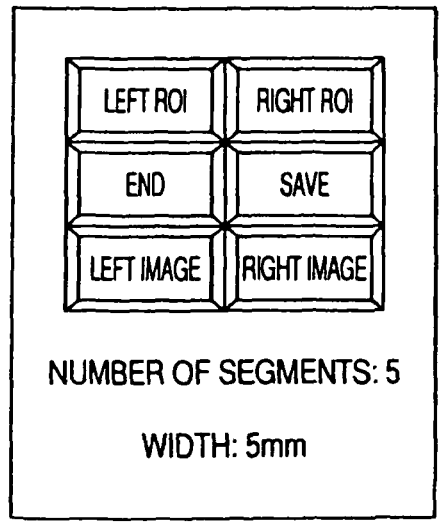

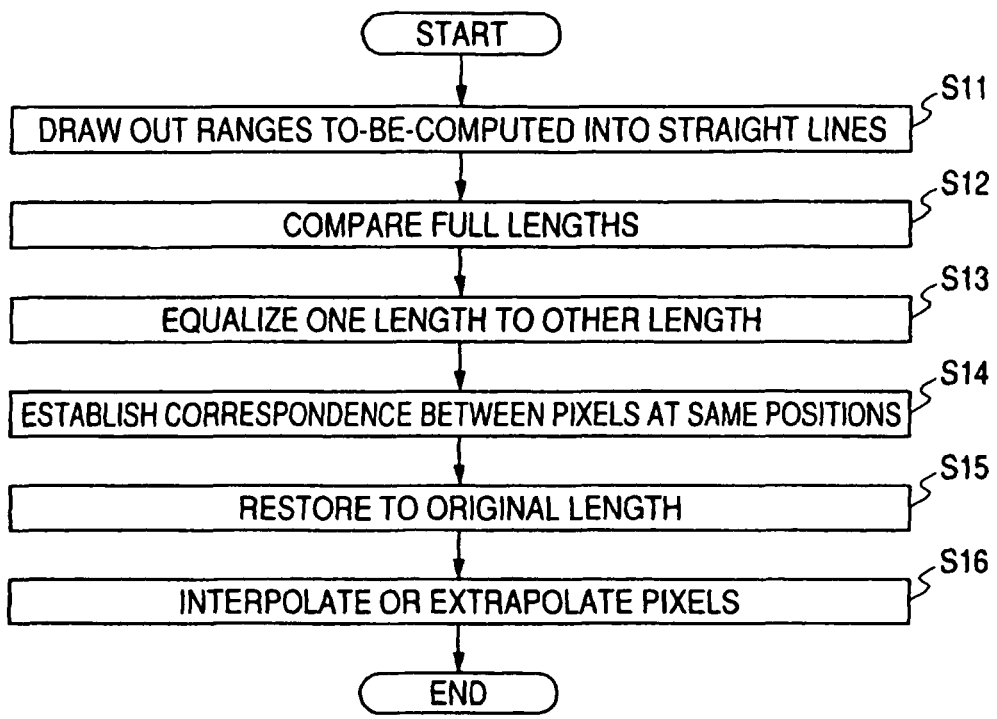
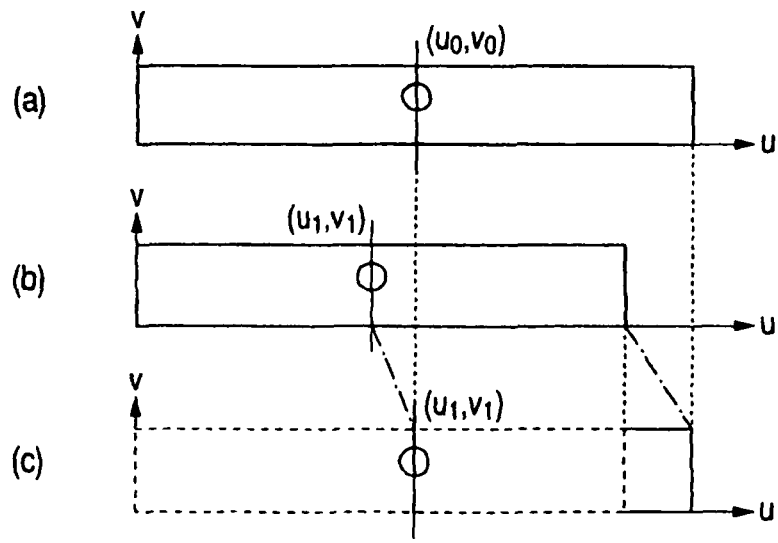

ULTRASONIC DIAGNOSTIC EQUIPMENT AND IMAGING PROCESSING APPARATUS

BACKGROUND OF THE INVENTION

1. Field of the Invention

The present invention relates to an ultrasonic diagnostic equipment and an image processing apparatus, and more particularly to an ultrasonic diagnostic equipment and an image processing apparatus which offer information reflective of the blood flow velocity of a myocardial tissue by employing contrast echoes.

2. Description of the Prior Art

In the field of ultrasonic diagnostic equipments, the spotlight of attention has recently been focused upon contrast echocardiography wherein, in examining the heart, an abdominal organ or the like, an ultrasonic contrast medium is injected from a vein so as to estimate a blood flow movement. The technique of injecting the contrast medium from the vein is less invasive than the technique of injecting the same from an artery, and diagnoses based on the estimation method are coming into wide use. The ultrasonic contrast medium is principally constituted by microbubbles, which form reflection sources reflecting ultrasonic signals. As the dose or density of the contrast medium is higher, a contrasting effect enlarges more. In relation to the property of the bubbles of the contrast medium, however, such a situation occurs that the duration of the contrasting effect is shortened by ultrasound projection.

In case of performing the contrast echocardiography, the contrast medium is successively supplied to the region of interest (ROI) of a patient part by a blood flow. It is therefore supposed that, even when the bubbles have been once caused to disappear by projecting an ultrasound, the contrasting effect will be maintained if new bubbles flow into the ROI at the time point of the next ultrasound projection. In actuality, however, ultrasounds are usually transmitted and received several thousand times in one second, and an organic parenchyma of low blood flow velocity or the blood flow movement of a comparatively fine blood vessel is existent. In consideration of these facts, the bubbles will disappear in succession before intensity enhancement based on the contrast medium is confirmed on the image of such a diagnosis, with the result that the contrasting effect will weaken instantly.

The most fundamental one of diagnostic method among those employing the contrast medium consists in that the amount or presence of the blood flow of the part to-be-diagnosed is found by checking the presence of the intensity enhancement based on the contrast medium.

Further, an imaging technique which is called "flash echo imaging method" (or also called "transient response imaging method") has been proposed by utilizing the phenomenon that the microbubbles disappear by the projection of the ultrasounds as stated above, and it has been reported that the intensity enhancement can be bettered by the imaging method (refer to, for example, Patent Document 1). In principle, the imaging method is a technique wherein the conventional continuous scan of, e.g., several tens frames in one second is replaced with the intermittent transmission of, e.g., one frame in several seconds. The microbubbles densified without being burst during the time interval of the intermittence are extinguished at one time, thereby intending to obtain a high echo signal.

In myocardial contrast echocardiography, however, enhancement is nonuniform due to nonuniformity in the acoustic field of a sector probe, and nonuniformity in an acoustic field as is induced by an in-vivo structure. The nonuniformity forms an obstacle to the diagnosis of myocardial ischemia or a myocardial infarction part.

Here, the "nonuniformity in the acoustic field of the sector probe" is as stated below. In the sector probe which is generally used in the examination of a circulatory organ employing an ultrasonic diagnostic equipment, transmission conditions are constant for individual scan lines constituting an image. Accordingly, when the deflection angle of a beam enlarges, there arise the phenomena in which a transmission acoustic field differs depending upon the scan lines, 1) that the acoustic pressure of the transmission beam formed on the scan line lowers, and 2) that a beam width becomes thicker than in a case where the transmission beam is not deflected, so a spatial resolution degrades.

In the prior-art B-mode scan of an ultrasonic beam, therefore, the endeavor of generating a more uniform image is made as a measure against the phenomena, by adopting such a technique as adjusting factor of the images such as a reception gain for every scan line on the basis of a reception signal from the nonuniform transmission acoustic field.

However, the above countermeasure is directed toward the case of the B-mode image, and it does not suppose the case of tissue harmonic imaging (THI) having come into the limelight in recent years, or harmonic imaging such as contrast echo imaging, so that drawbacks as stated below are involved.

In the harmonic imaging, the transmission acoustic field, especially the acoustic pressure, becomes an important factor for a sensitivity, and it has its limit to correct the nonuniformity of the transmission acoustic field by the image adjustments of the reception. Therefore, the uniformity of the transmission acoustic field is required for satisfactorily demonstrate the effects of the adjustments. The reason therefor is that, since the intensities of harmonic components are proportional to the square of the acoustic pressure, the reception gain the amplitude of which is the square of that in the prior-art B-mode must be corrected, so the change of a noise level is induced by the change of the reception gain, whereby a nonuniform image in which the noise level differs is generated.

Besides, irrespective of the harmonic imaging, the beam width generally thickens when the deflection angle of the transmission beam enlarges. This phenomenon induces the nonuniformity of the spatial resolution. Especially in a case of parallel simultaneous receptions, the phenomenon of beam bends might be increased.

On the other hand, the "nonuniformity of the acoustic field attributed to the in-vivo structure" is induced in such a manner, for example, that a rib exists in close proximity to the probe, so the transmission and reception of ultrasounds are hampered by the rib. In particular, since part of the left ventricle is located so as to be covered with the left lung, the lung intervenes between the probe and the myocardium, to often bring about the result that the corresponding part darkens on an image obtained by an ultrasonic diagnosis (refer to FIG. 1A).

Among the nonuniformities, the nonuniformity of the acoustic field of the sector probe can be theoretically corrected, but the nonuniformity of the acoustic field which is induced by the in-vivo structure cannot be corrected for the reason that the structure differs depending upon patients, so a theoretical solution does not exist. Therefore, it becomes difficult to detect a morbid part, such as myocardial ischemia or myocardial infarction part, which is clinically to be found.

Meanwhile, a technique for diagnosing the ischemic malady of the heart is called "stress echocardiography". The technique is such that a vasodilator drug, for example, ATP (adenosine triphosphate) is injected into the myocardium by an intravenous drip or the like so as to expand blood vessels, whereupon a contrast medium is injected instead of the vasodilator drug, thereby intending to obtain an ultrasonic image.

According to the technique, a normal part becomes brighter than before because the blood vessels expand thereat. On the other hand, a morbid part undergoes the steal phenomenon of darkening contrariwise, for the reason that, since the blood vessels are difficult to expand at the morbid part, a blood flow increases to surrounding blood vessels which have expanded.

In a case where the blood vessels are not completely closed and where they become fine, a chest pain is sometimes incurred by a violent motion. In this regard, the technique is intended to observe such a part appearing as a defect (refer to FIG. 1B).

Even with this method, however, parts I' and II' sometimes seem to be ischemic regions as shown in FIG. 1B by way of example. That is, even with the stress echocardiography, it is very difficult to judge an ischemic region from a single image.

In order to solve such problems, a method is considered in which ultrasonic images of two or more frames are taken so as to be compared and studied. For this purpose, after the first image has been first obtained by injecting the contrast medium, the second image is taken by injecting the vasodilator drug and expanding the blood vessels, whereupon both the images are compared. Even with this method, however, the visual inspection of a diagnostician has its limit, and if a certain part is morbid is disputable and suspicious. Therefore, a method for comparing and arithmetically operating the two images is required. It is an actual situation to fulfill the requirement by executing the arithmetic operation between the different images.

Such an arithmetic operation is digital subtraction in which the images of the two frames are subjected to differential processing (refer to, for example, Japanese Patent No. 3,023, 290). This method, however, is employed in a case where the temporal difference between the two B-mode images is usually correspondent to several frames, that is, about 1/20-1/10 second in terms of time, so that it is hardly influenced by the pulsatory motion of an internal organ, the motion of a probe, or the like. Accordingly, only echoes caused by the contrast medium can be displayed on the differential image between the images of the two frames.

In contrast, especially in the stress echocardiography which compares the images before and after the stressing, a time interval is greater than in the mere flash echo imaging whose time interval is as short as several cardiac beats, and the positional shifts of the heart attributed to the motion of a patient himself/herself, how to apply the probe, etc. are not negligible. When the arithmetic operation is directly executed without making positional corrections, such a situation takes place where a motion artifact appears or where quite no operated result is obtained.

Further, ROIs (regions of interest) need to be separately set for the two images. In this regard, in a case where both the set ROIs are inaccurate, that is, where they do not satisfactorily correspond to each other, an accurate operated result cannot be expected.

SUMMARY OF THE INVENTION

The present invention has been made in consideration of the above circumstances, and has for its object to provide an ultrasonic diagnostic equipment and an image processing apparatus which can compare images before and after stressing more accurately.

Another object of the invention is to provide an ultrasonic diagnostic equipment and an image processing apparatus which can set ROIs accurately and easily.

Still another object of the invention is to provide an ultrasonic diagnostic equipment and an image processing apparatus in which operated results are easily visible.

First, the fundamental concept of an arithmetic operation as is one aspect of the invention will be elucidated with reference to FIG. 1. In the invention, an imaging method, for example, what is called "flash echo imaging" is used for acquiring images. As stated before, the flash echo imaging is a technique wherein echo signals of high intensities are acquired in such a way that microbubbles (a contrast medium) densified in an internal organ without being burst are extinguished at one time by intermittently transmitting an ultrasonic beam. In other words, the technique of this aspect of performance consists in that the microbubbles forming the contrast medium are positively disintegrated with a certain regularity, thereby intending to obtain an efficient diagnostic image. Incidentally, the ultrasonic contrast medium should preferably be given by continuous intravenous drip infusion, and the contrast echo imaging based on the dripped contrast medium is carried out.

FIG. 1A simulates the image of the heart before stressing, that is, before the injection of a vasodilator drug as has been obtained in conformity with flash echo imaging by injecting a contrast medium. In this example, the heart is divided into six parts I through VI, and only the part I of them is dark. Only with the image, however, it cannot be judged whether the darkening is ascribable to ischemia or to the influence of the lung or decay.

On the other hand, FIG. 1B simulates the image of the heart as has been obtained by injecting the contrast medium again after the stressing, that is, after the injection of the vasodilator drug. When FIGS. 1A and 1B are compared, parts III' through VI' are brighter than before the stressing, and it is seen that blood has increased owing to the expansion of blood vessels. In contrast, a part II' is darker than before the stressing. Therefore, whereas the blood vessels of a normal part have expanded owing to the injection of the vasodilator drug, a morbid part can be estimated to have undergone a steal phenomenon in which a blood flow worsens contrariwise.

With respect to a part I', although the part I' is brighter than the part I before the stressing, it is darker than the parts III' etc. It cannot be concluded whether the darkening is ascribable to ischemia or to the influence of the lung or the decay of ultrasounds.

Herein, when note is taken of the fact that the stressing brightens the normal region and darkens the ischemic region, a difference, for example, obtained by subtracting an intensity before the stressing from an intensity after the stressing becomes a plus value at the normal part without fail and becomes a minus value at the ischemic part without fail, so that both the parts can be definitely distinguished. Besides, a quotient obtained by dividing the intensity after the stressing by the intensity before the stressing becomes a value greater than one at the normal part without fail and becomes a value less than one at the ischemic part without fail, so that both the parts ought to be similarly distinguishable definitely.

FIG. 1C shows results obtained by such arithmetic operations. In the light of the results, even when any of the normal parts is influenced by the lung or the decay of ultrasounds, a brighter operated result is obtained at the pertinent normal part as at the other normal parts. In contrast, a darker operated result is obtained at the ischemic part irrespective of the presence or absence of such an influence, and the difference of the ischemic part from the normal parts is displayed more definitely.

The above is the most characterizing aspect of the invention. Other aspects, for example, means for positioning two images, and means for setting ROIs are adopted in the invention in order to incarnate the fundamental concept more accurately and easily.

In order to accomplish the objects mentioned before, an ultrasonic diagnostic equipment according to one invention of the present application consists concretely in comprising image acquisition means for acquiring image data by scanning a patient into whom an ultrasonic contrast medium has been injected, with ultrasonic beams; same-part correspondence means for bringing same parts into correspondence with each other, between a plurality of images concerning the same parts of the identical patient and taken by the image acquisition means; arithmetic operation means for arithmetically operating image information items on changes of intensities between the plurality of images by using the intensities of those mutually corresponding pixels of the plurality of images which have been brought into correspondence by the same-part correspondence means; and display means for displaying results operated by the arithmetic operation means. Besides, such a construction can be realized also in an image processing apparatus.

The arithmetic operation means should preferably include inverse-transformation arithmetic-operation means for transforming ultrasonic signals acquired by the image acquisition means and subjected to logarithmic compression, onto a linear scale, and it may well be constructed so as to further include compensation means for comparing the intensities of heart cavity parts of the individual images and then compensating for the intensities between the respective images.

Next, an ultrasonic diagnostic equipment according to another invention of the present application comprises processing means for processing data of a plurality of images taken for same parts of an identical patient into whom an ultrasonic contrast medium has been injected, in conformity with a predetermined algorithm; same-part correspondence means for bringing the same parts into correspondence with each other, between the plurality of images; arithmetic operation means for arithmetically operating image information items on changes of intensities between the plurality of images by using the intensities of those corresponding pixels of the plurality of images which have been brought into correspondence by the same-part correspondence means; and display means for displaying results operated by the arithmetic operation means.

Besides, an ultrasonic diagnostic equipment according to still another invention of the present application comprises image acquisition means for acquiring image data by scanning a patient into whom an ultrasonic contrast medium has been injected, with ultrasonic beams; first display means for displaying the image data; ROI setting means for setting ROIs (regions of interest) on images displayed by the first display means; same-part correspondence means for bringing same parts into correspondence with each other, between the plurality of images concerning same parts of the identical patient and acquired by the image acquisition means, as to the ROIs; arithmetic operation means for arithmetically operating image information items on changes of intensities between the plurality of images by using the intensities of those corresponding pixels of the plurality of images which have been brought into correspondence by the same-part correspondence means; and second display means for displaying results operated by the arithmetic operation means.

Here, the same-part correspondence means can preferably include measurement means for measuring full lengths of the ROIs respectively set on the plurality of images which concern the same parts of the identical patient and which have been taken by the image acquisition means; expansion/contraction means for increasing or decreasing the full length of one of the set ROIs so as to be equalized to the full length of the other ROI; identification means for identifying the pixels at equal distances from one end in a case where the ROIs are open, or from a specified point in a case where the ROIs are closed, to be the pixels which lie at the same positions; restoration means for restoring the lengthened or shortened ROI to its original length; and specification means for specifying the individual pixels of the ROI restored to its original length by the restoration means, and the corresponding pixels of the ROI before the restoration.

Besides, the ROI setting means can be preferably constructed so that the ROI setting means includes segmentation means for dividing each of the ROIs on the plurality of images set by the ROI setting means, into a plurality of segments associated between the plurality of images, and that the first display means has a function of displaying the segments divided by the segmentation means, on the ROIs. In this case, more preferably, the segmentation means may divide a contour of an imaged heart or myocardial region of the patient into three segments of a base part, a middle part and an apex part in correspondence with left and right valvular rings and an apex of the heart, respectively, so as to set and display the segments on the ROI, or it may well divide a contour extending from a left valvular ring via an apex of the heart to a right valvular ring, in an imaged heart or myocardial region of the patient, into five segments of a left base part, a left middle part, an apex part, a right middle part and a right base part, respectively, so as to set and display the segments on the ROI.

Alternatively, the ROI setting means can preferably set the ROI by automatically subjecting a plurality of chosen points to curve fittings, and it can further reset the ROI in such a way that, when the plurality of chosen points are moved, the corresponding curve fittings are automatically caused to follow the movements.

Meanwhile, the first display means is preferably capable of displaying the plurality of images in parallel, and the second display means displays results operated by the arithmetic operation means, in colors, and it is capable of displaying a color map in association with the operated results in the ROI set by the ROI setting means, and/or it is capable of displaying blood flow velocities of relatively smaller values as operated by the arithmetic operation means, in colors which express lower velocities in a predetermined color bar, and blood flow velocities of relatively larger values in colors which express higher velocities in the color bar.

Further, the arithmetic operation means may execute arithmetic operations for the plurality of images concerning the same parts of the identical patient, the images being taken before and after giving a vasodilator drug by the image acquisition means and execute the arithmetic operations by employing an algorithm which measures coronary reserve bloods of the individual pixels in the ROIs set by the ROI setting means, or the arithmetic operation means may well execute arithmetic operations for the plurality of images concerning the same parts of the identical patient, the images being taken after giving a vasodilator drug by the image acquisition means, execute the arithmetic operations between the images of different intermittent intervals and execute the arithmetic operations by employing an algorithm which evaluates mean blood supply velocities of the individual pixels in the ROIs set by the ROI setting means.

As described above, in accordance with the ultrasonic diagnostic equipment and the image processing apparatus according to the invention, the images before and after stressing can be compared more accurately.

Moreover, in accordance with the ultrasonic diagnostic equipment and the image processing apparatus according to the invention, the ROIs can be set accurately and easily.

Furthermore, the invention has the advantage of obtaining the ultrasonic diagnostic equipment and the image processing apparatus in which the operated results are easily visible.

BRIEF DESCRIPTION OF THE DRAWINGS

In the accompanying drawings:

FIGS. 1A-1C are diagrams for elucidating the concept of the present invention, wherein FIG. 1A is an image before the injection of a vasodilator drug, FIG. 1B is an image after the injection of the vasodilator drug, and FIG. 1C is an image showing the result of the operation between both the images before and after the injection;

FIG. 3 is a flow chart showing the outline of a process for setting ROIs;

FIG. 4 is a diagram showing a controlling window which is used for setting the ROIs;

FIG. 9 is a flow chart showing the outline of a process for bringing into correspondence the pixels of the image before the stressing and the image after the stressing;

FIG. 10 is a conceptual diagram for explaining the operation of bringing into correspondence the pixels of the image before the stressing and the image after the stressing;

DETAILED DESCRIPTION OF THE PREFERRED EMBODIMENTS

Now, the first embodiment of this invention will be described with reference to the drawings as to an ultrasonic diagnostic equipment in which the data of a blood flow movement are obtained on the basis of the degree of enhancement of a contrast medium flowing into a myocardium, so as to identify an abnormal part. Incidentally, the ultrasonic diagnostic equipment according to the invention is also applicable to any region of interest, an abdominal or other organs, for example, the liver in a case where the ultrasonic contrast medium is given to a patient and where a blood flow state is observed on the basis of the degree of enhancement.

Figure 2:
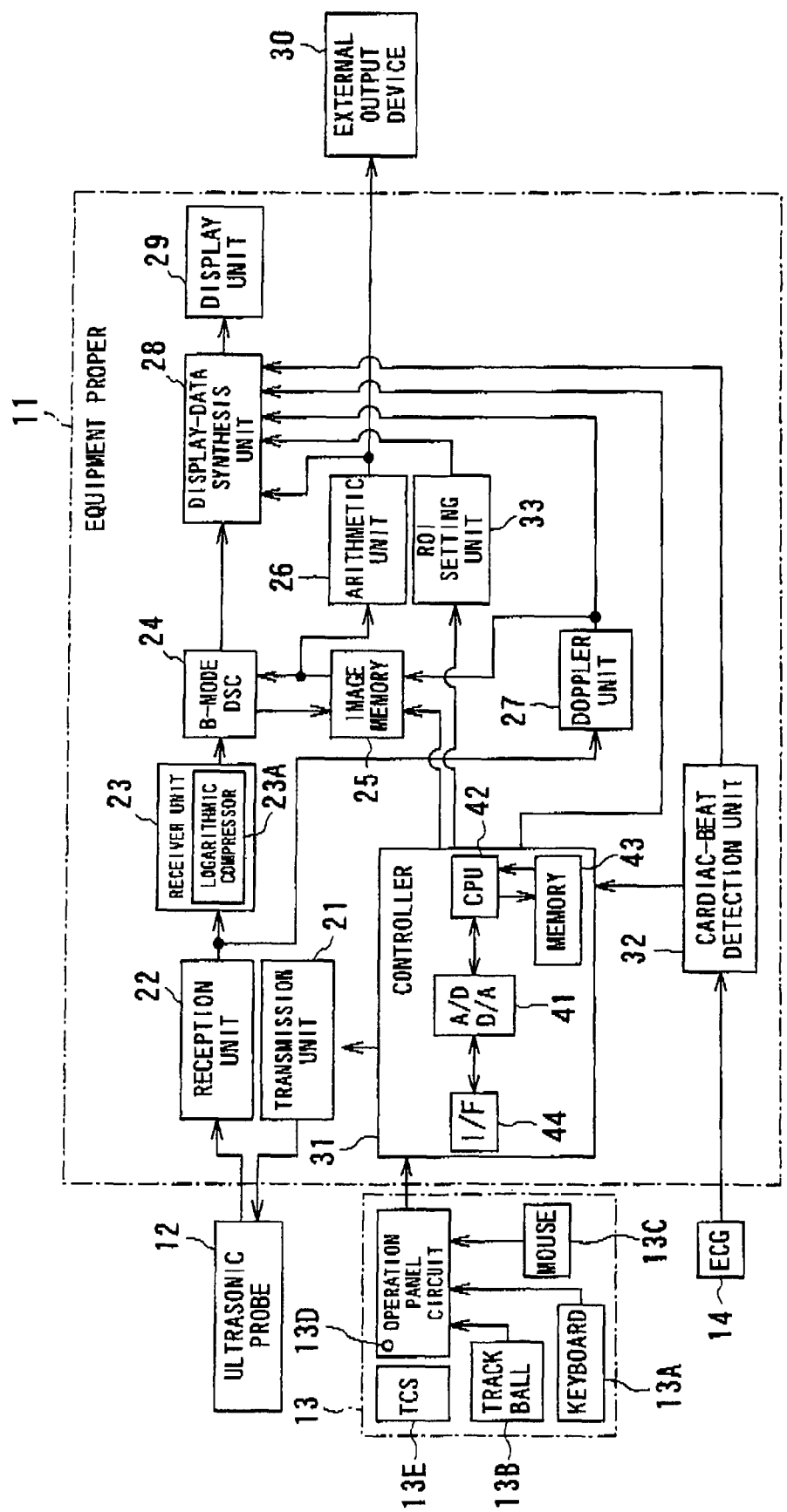
FIG. 2 is a block diagram of an ultrasonic diagnostic equipment according to the first embodiment of the invention.

FIG. 2 schematically shows the general construction of the ultrasonic diagnostic equipment according to the first embodiment. The ultrasonic diagnostic equipment shown in FIG. 2 includes the equipment proper 11, and an ultrasonic probe 12, an operation panel 13 and an ECG (electrocardiograph) 14 which are connected to the equipment proper 11.

The operation panel 13 is used for giving various instructions and information items to the equipment proper 11 by an operator. This operation panel 13 includes a keyboard 13A, a track ball 13B, a mouse 13C, an operation start button 13D which serves to start an arithmetic operation to be stated later, and a TCS (Touch Command Screen) 13E which is operated in direct finger touch. The track ball 13B functions as, for example, a pointing device on a monitor screen, and it is also used for setting an ROI (region of interest) on an image, etc. When the keyboard 13A, etc. are operated, an instruction can be given for changing-over an imaging mode between "B-mode imaging" and "CFM (Color Flow Mapping)-mode imaging". The CFM-mode imaging is the imaging mode which displays the blood flow state as a two-dimensional color image, and in which an image of CFM-mode is displayed in superposition on an image of B-mode.

The ultrasonic probe 12 is a device which bears the transmission and reception of ultrasonic signals to and from the patient, and which has piezoelectric vibrators of piezoelectric ceramics or the like as electric/mechanical reversible transducers. As a preferable example, the probe of phased array type 12 is constructed by arraying the plurality of piezoelectric vibrators and disposing them at a distal probe end. Thus, the probe 12 converts pulse drive voltages applied by the equipment proper 11, into ultrasonic pulse signals and then transmits the pulse signals in desired directions within the patient, while it converts ultrasonic echo signals reflected from the patient, into echo signals of corresponding voltages.

The ECG 14 is chiefly used in touch with the skin of the body of the patient, so as to obtain the electrocardiogram waveform data of the patient.

As shown in the figure, the equipment proper 11 includes a transmission unit 21 and a reception unit 22 which are connected to the probe 12, and a receiver unit 23, a B-mode DSC (digital scan converter) 24, an image memory 25, an arithmetic unit 26, a Doppler unit 27, a display-data synthesis unit 28, an ROI (region of interest) setting unit 33 and a display unit 29 which are located on the output side of the reception unit 22. Connected to the arithmetic unit 26 is an external output device 30 which is located outside the diagnostic equipment. The external output device 30 is constructed of, for example, a printer, a magnetic storage medium, or/and a personal computer which is arranged via a network. The equipment proper 11 further includes a controller 31 which serves to control the transmission timings of the ultrasonic signals from the transmission unit 21, and a cardiac-beat detection unit 32 which accepts an ECG (electrocardiogram) signal detected by the ECG 14.

The constructions and operations of the individual circuits of the equipment proper 11 will be further described.

The transmission unit 21 has a pulse generator, a transmission delay circuit and a pulser which are not shown. The pulse generator generates rate pulses at a rate frequency fr [Hz] of, for example, 5 kHz (period: 1/fr [second]). The rate pulses are distributed in the number of channels, and are sent to the transmission delay circuit. The transmission delay circuit is fed with a timing signal for determining a delay time, every transmission channel. Thus, the transmission delay circuit endows the rate pulse with the command delay time every channel, and the rate pulse endowed with the delay time is fed to the pulser every transmission channel. The pulser impresses a voltage pulse every piezoelectric vibrator (transmission channel) of the probe 12 at a timing at which it has received the rate pulse. Thus, the ultrasonic signal is emitted from the probe 12. The ultrasonic signal transmitted from the ultrasonic probe 12 is focused into the shape of a beam within the patient, and has its transmission directivity set in a commanded scan direction.

In this manner, the ultrasonic pulse signal is transmitted through the probe 12 by the drive of the transmission unit 21, and its timing is controlled by the transmission controller 31.

The beam is formed in accordance with the above delay time within the patient. The transmitted ultrasonic pulse signal is reflected from the discontinuous plane of an acoustic impedance within the patient. The reflected ultrasonic signal is received by the probe 12 again, and is converted into the echo signal of corresponding voltage magnitude. The echo signal is accepted from the probe 12 into the reception unit 22 every reception channel.

The reception unit 22 includes a preamplifier, a reception delay circuit and an adder in succession as viewed from the input side thereof. Each of the preamplifier and the reception delay circuit has built-in amplifier circuits or delay circuits in the number of reception channels. The delay times of the reception delay circuit are given as signals in a delay time pattern, in conformity with a desired reception directivity. Therefore, the echo signal is amplified every reception channel by the preamplifier and is endowed with the delay time by the reception delay circuit. Thereafter, such echo signals are added up by the adder. Owing to the addition, a reflection component from a direction conforming to the desired reception directivity is enhanced. The overall performance of the ultrasonic beams of the transmission and reception is obtained by putting the performances of the transmission directivity and reception directivity together.

The output node of the adder of the reception unit 22 leads to the display-data synthesis unit 28 via the receiver unit 23 and the B-mode DSC 24 in succession.

The receiver unit 23 includes a logarithmic compressor 23A, an envelope detector and an A/D converter though some of them are not shown. By the way, in a case of an equipment which performs a harmonic imaging method, the receiver unit 27 is additionally furnished with a band-pass filter which passes only a higher harmonic component being, for example, twice as high as the transmission frequency of the ultrasonic pulse signals. Owing to the receiver unit, echo data in the direction in which the reception directivity has been given are formed in a digital quantity, and they are sent to the B-mode DSC 24.

The B-mode DSC 24 converts the echo data from a raster signal string of ultrasonic scan into a raster signal string of video format, and sends the resulting raster signal string to the display-data synthesis unit 28.

The image memory 25 is connected to the B-mode DSC 24, and it includes a memory device for recording the processing signal of the DSC (either the raster signal string of ultrasonic scan or the raster signal string of video format) therein, and a write/read control circuit for the memory device. The echo data recorded in the memory device are read out in frame units during or after imaging. The read-out data are sent to the display unit 29 via the B-mode DSC 24 as well as the display-data synthesis unit 28, and are displayed thereon.

Besides, the read output node of the image memory 25 is connected to the arithmetic unit 26, whereby the read-out data from the memory are acceptable into the arithmetic unit 26. The arithmetic unit 26 includes a work memory, and an arithmetic circuit such as CPU. It performs an arithmetic operation to be stated later, on the basis of the echo data loaded into the work memory, and it can deliver the operated data to the display-data synthesis unit 28, and to the external output device 30 as may be needed. Thus, the operated result is displayed on or delivered to the display unit 29 and the external output device 30.

The Doppler unit 27 receives the added echo signals processed by the reception unit 22. This unit 27 includes an orthogonal detector, an A/D converter, an anti-clutter filter, a Doppler-shift-frequency analyzer, an arithmetic unit for a mean velocity, etc., a DSC, a color processing circuit, and so forth, though they are not shown. Thus, Doppler shift frequencies, in other words, the velocity information and power information of a blood flow, etc. are obtained as color flow mapping data (CFM data). The color flow mapping data are subjected to noise canceling and the like processes and have their scan scheme converted by the built-in DSC of the Doppler unit 27, whereupon the resulting data are sent to the display-data synthesis unit 28. The color flow mapping data can also be sent to the image memory 25 so as to be stored therein.

The ROI setting unit 33 receives ROI setting information items (ROI position, size and shape) outputted from the operation panel 13 including the track ball 13B, etc., and it outputs ROI setting signals (including the graphic data of a ROI) corresponding to the received information items, to the display-data synthesis unit 28. Therefore, the ROI (region of interest) of desired shape and size can be set at a desired position on the screen of the display unit 29 in such a way that the observer operates the operation panel 13 while observing the screen.

The cardiac-beat detection unit 32 receives the ECG signal fed from the ECG 14 and sends the ECG waveform data to the display-data synthesis unit 28 so as to display them, while it creates a cardiac-beat signal synchronized with an R-wave for cardiac synchronization and sends the cardiac-beat signal to the transmission controller 31.

The display-data synthesis unit 28 performs processing such as arranging or superposing the B-mode image data (gray scale image) sent from the B-mode DSC 24, the CFM-mode image data (color flow image) sent from the Doppler unit 27, the electrocardiogram waveform data sent from the cardiac-beat detection unit 32, the arithmetic data of the arithmetic unit 26, the graphic data of the ROI sent from the ROI setting unit 33, and/or desired setting parameters, thereby to reconstruct the data into image data of one frame. The frame image data are sequentially readout by the display unit 29. In the display unit 29, the image data are converted into an analog quantity by a built-in D/A converter, so as to display the tomogram of the tissue shape of the patient on a display device such as TV monitor.

Further, the controller 31 includes an A/D converter 41 for accepting an operation signal from the operation panel 13, and a CPU (central processing unit) 42, and besides, a memory 43 connected to the CPU 42. Prestored in the memory 43 are a protocol which serves to set the protocol (here, "transmission timing string") of an intermittent transmission method based on a flash echo imaging method, and a program which executes a scan sequence in accordance with the protocol. The CPU 42 is connected to the operation panel 13, cardiac-beat detection unit 32, transmission unit 21, ROI setting unit 33 and image memory 25 through the A/D-D/A converter 41 and an interface 44, and it performs processes to be stated later.

Subsequently, there will be described operations in the case where image data are acquired by the ultrasonic diagnostic equipment 11, that is, in the case where the ultrasonic diagnostic equipment operates as an ordinary ultrasonic imaging apparatus.

First, the transmission unit 21 drives the probe 12 on the basis of the delay time control of the CPU 42 so as to implement, for example, electronic sector scan based on ultrasonic beams. Echo signals from within a patient as have been obtained by the scan are passed through the probe 12 again, and are inputted to the reception unit 22 as signals of electric quantity. The echo signals are subjected to reception focusing by the delay time control of the CPU 42 in the reception unit 22, and are thereafter sent to the B-mode DSC 24 and/or the Doppler unit 27.

In the B-mode DSC 24, the B-mode tomogram data of ultrasonic scattering intensity are generated owing to the construction and functions described before. In the case of the CFM-mode, the two-dimensional distribution image data of a blood flow in a scanned section are generated.

An examiner gives the command of a scan mode desired to be observed, to the B-mode DSC 24 through the CPU 42. Thus, the B-mode DSC 24 recognizes the scan mode and alters the scan scheme of image data in that mode from an ultrasound scheme to a standard TV scheme, and the display-data synthesis unit 28 performs image synthesis in conformity with the scan mode. An image here is displayed by the monitor of the display unit 29. As a result, an image in the B-mode alone, or a blood-flow distribution image whose background image is the B-mode tomogram is displayed.

Meanwhile, referring back to the foregoing processing, in a case where an operation mode="Measurement mode" has been judged on the basis of the operation information of the examiner, the ultrasonic diagnostic equipment is operated as the image processing apparatus.

Next, operations in the case where image data are measured by the ultrasonic diagnostic equipment 11, that is, in the case where the ultrasonic diagnostic equipment operates as an image processing apparatus, will be described with reference to FIG. 3.

First, the CPU 42 invokes a first image stored in the image memory 25 (in this case, an image taken before stressing, that is, before the injection of a vasodilator drug), in compliance with the instruction of an examiner from the operation panel 13 (step S1), so as to display the invoked image on the display unit 29 (step S2). In this case, when there are a plurality of images taken before the stressing, an appropriate image is selected through the operation panel 13 by the examiner. An instruction from the operation panel 13 in this case is given in such a way that a "Right image" button on a controlling window shown in FIG. 4, for example, is clicked by the mouse 13C.

Figure 5:
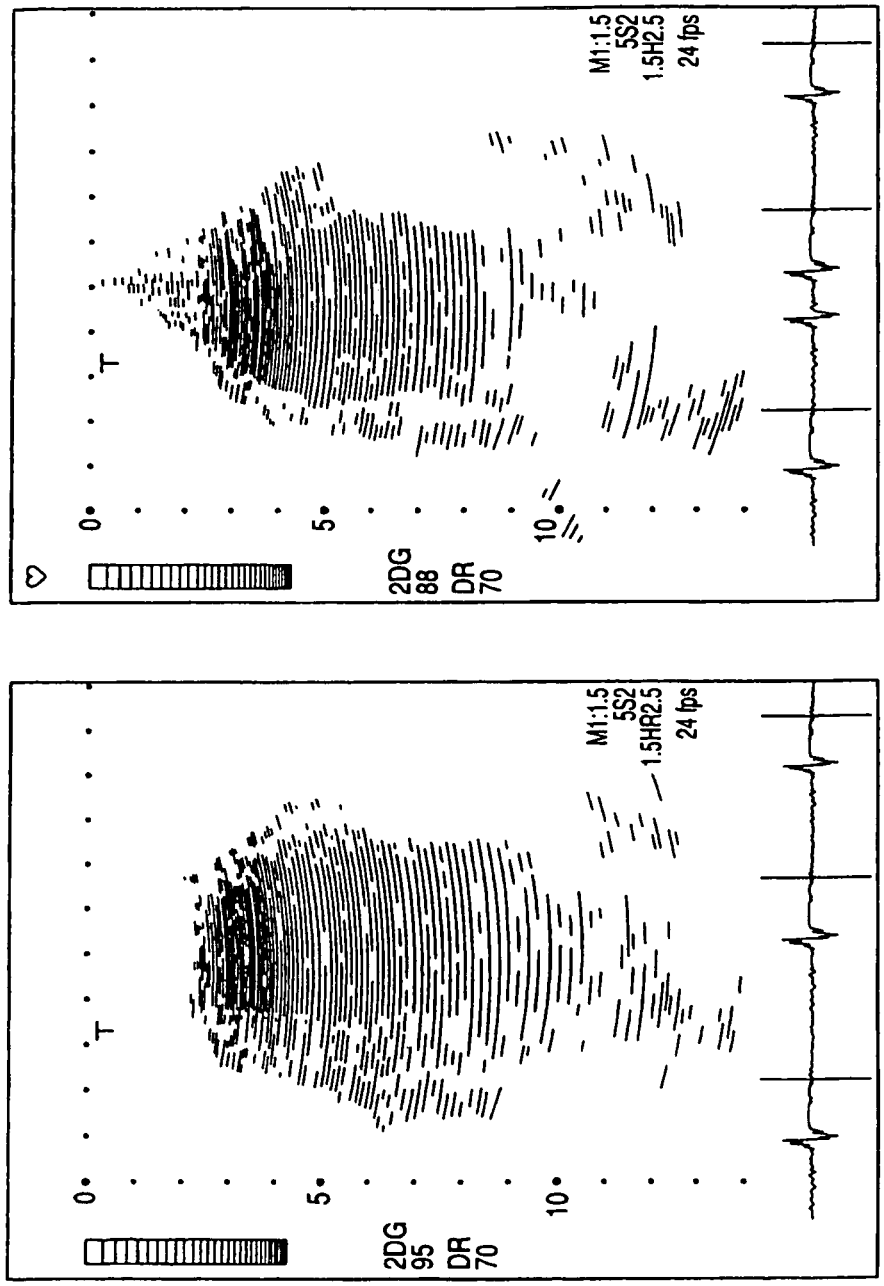
FIG. 5 is a diagram showing images before stressing and after the stressing as are displayed in parallel on a monitor.

When the image before the stressing is displayed, the CPU 42 subsequently invokes a second image stored in the image memory 25 (in this case, an image taken after the stressing, that is, after the injection of the vasodilator drug), in compliance with the instruction of the examiner from the operation panel 13 (step S3), so as to display the invoked image on the display unit 25 (step S4). In this case, when there are a plurality of images taken after the stressing, an appropriate image is selected through the operation panel 13 by the examiner. In this manner, the images before and after the stressing are displayed in parallel on the screen of the monitor of the display unit 29 (refer to FIG. 5).

The CPU 42 subsequently loads the operation signals of the examiner from the operation panel 13, so as to send ROI setting signals corresponding to the operation signals to the ROI setting unit 33 and the arithmetic unit 26 (step S5).

Figure 6:
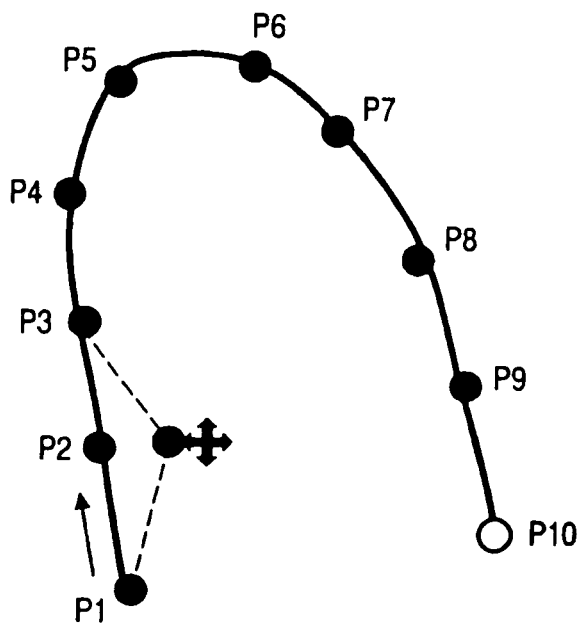
FIG. 6 is a diagram for explaining the setting and correction of the ROI.

Here, the setting of a ROI will be described with reference to FIG. 6. The operator first clicks the "Right ROI button" of the controlling window on the image displayed on the monitor of the display unit 29, thereby to enter a ROI setting mode. Besides, the operator moves the track ball or the like of the operation panel 13 to that point of the left valvular ring or right valvular ring at which the interior of the cardiac wall is clear, and he/she presses a setting button, thereby to set the starting point (P1) of the ROI. Thereafter, he/she sets the points at which the inner side of the cardiac wall is clear, in succession by moving the track ball from the valvular ring to the apex of the heart (P2-P5). When the apex of the heart has been reached, he/she continues such operations toward the opposite valvular ring (P6-P9). Besides, when the opposite valvular ring has been reached, the last point (P10) is settled by, for example, double-clicking the setting button. In a case where the ROI is defined by a closed curve, he/she returns to the first point and clicks this point, thereby to settle the last point. Incidentally, the ROI can also be automatically set on the basis of the intensity values of the image.

The set points are connected in such a way that curve fitting is executed by known mathematical algorithms saved in the ROI setting unit 33, under the control of the CPU 42. Besides, the set points are displayed even after the ROI setting, and any of them can be moved by dragging it with the track ball or the like. With the movement of the set point, a curve for setting the ROI is also recomputed and corrected (step S6). When the satisfactory ROI has been set in this way, the operator saves this ROI in association with the pertinent image by clicking the "Save" button of the controlling window. When the "Left ROI" button of the controlling window is subsequently clicked, the setting of a ROI is permitted also for the left image.

Figure 7:
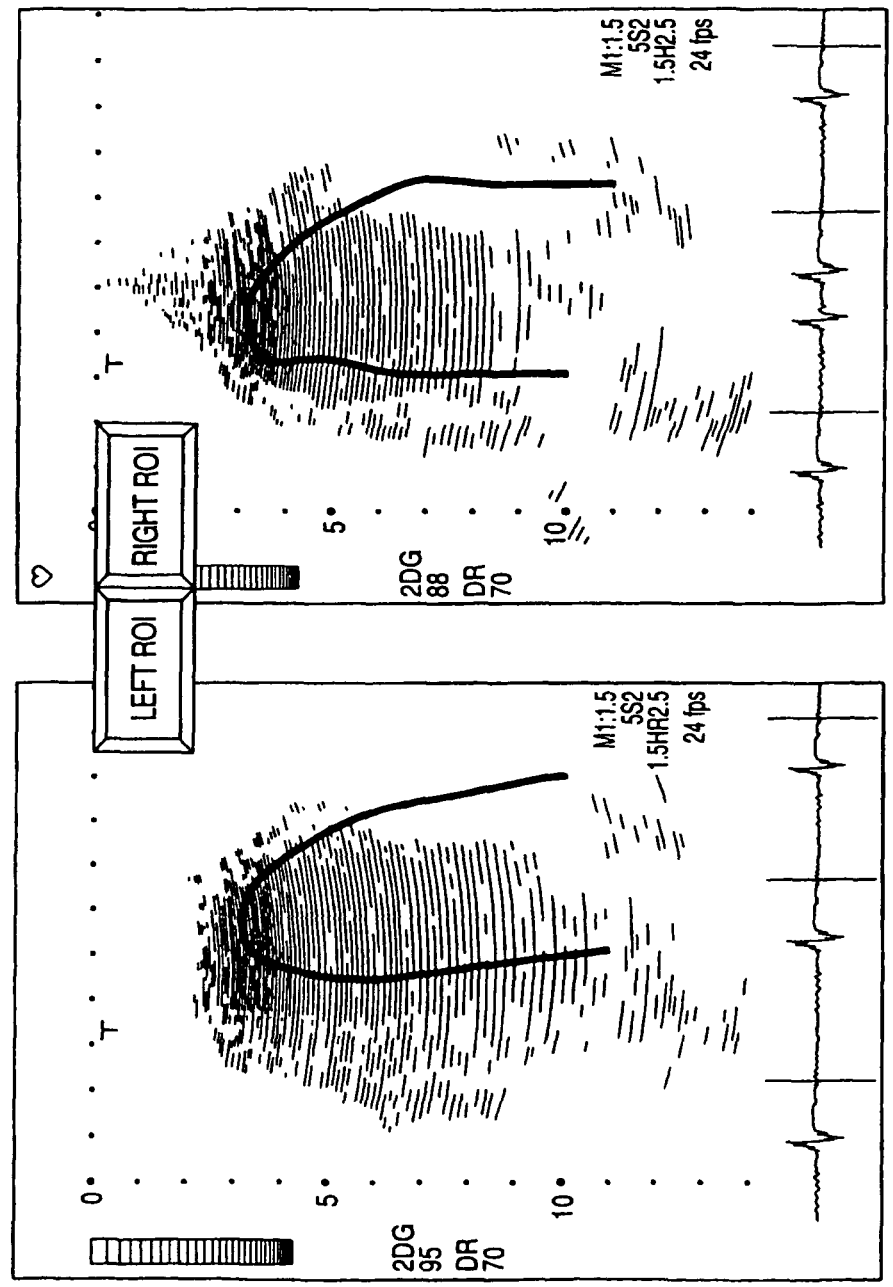
FIG. 7 is a diagram showing the set ROIs.

Thus, the ROIs of desired positions, sizes and shapes are set on the screen of the monitor of the display unit 29 as shown in FIG. 7 by way of example. Simultaneously, the information items of the positions, sizes and shapes of the ROIs are sent to the arithmetic unit 26.

Figure 8:
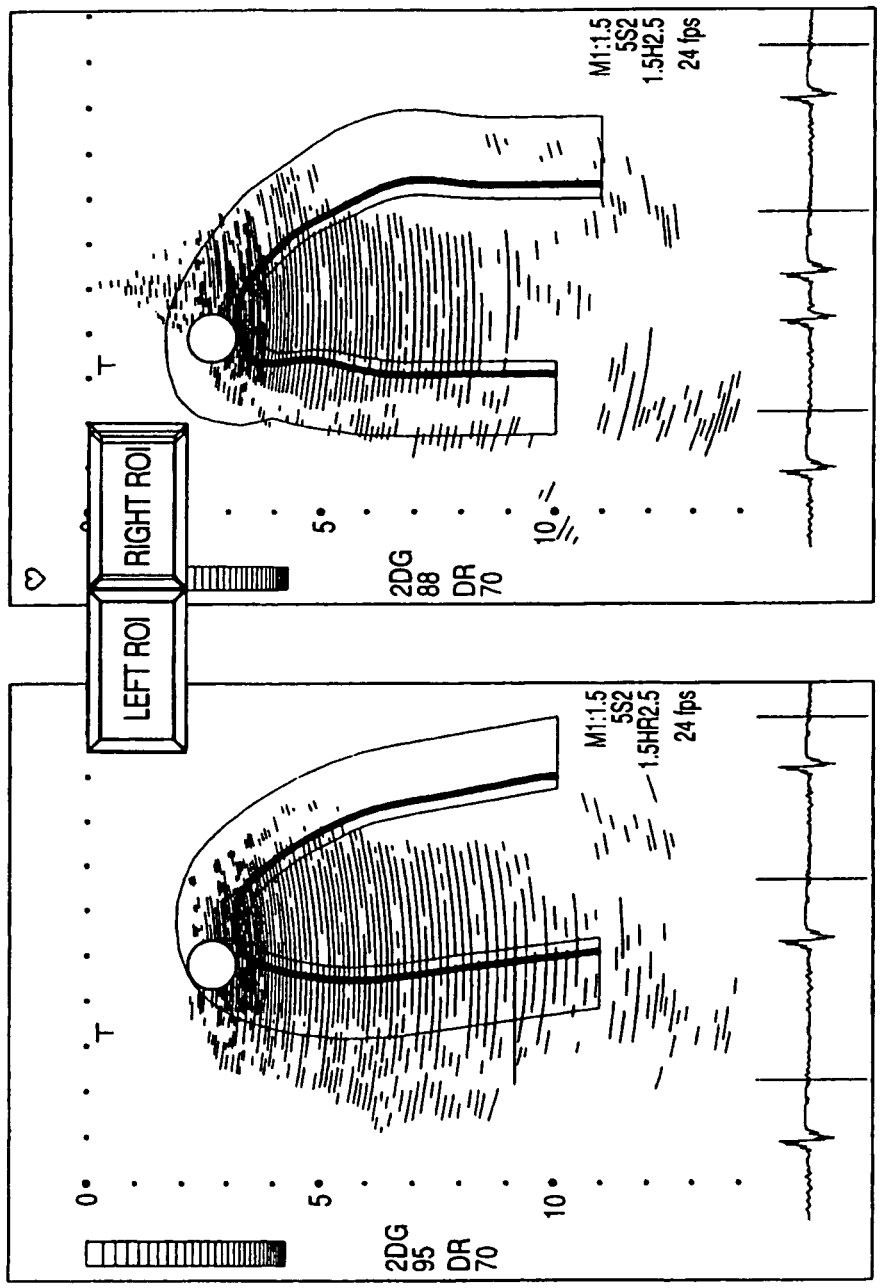
FIG. 8 is a diagram showing set ranges to-be-computed.

The CPU 42 further sends a command for setting ranges where the blood flow velocity of the myocardial tissue is to be computed, to the arithmetic unit 26 in compliance with the instruction of the examiner from the operation panel 13 (step S9). Although the ranges can also be set by the same steps as in the ROI setting, they are set by extracting ranges each of which extends a predetermined distance (about 5 mm to 1 cm) outside the set ROI as shown in FIG. 8.

Thus, the ROIs and the ranges to-be-computed can be set accurately and easily. Also, even when any error has developed in the course of the settings, the ROIs and the ranges to-be-computed can be easily corrected without redoing the settings.

Moreover, since only the parts necessary for the arithmetic operation can be easily extracted, a wasteful time period ascribable to the computations of unnecessary parts is omitted.

Subsequently, the CPU 42 commands the arithmetic unit 26 to execute a process in which corresponding pixels within the range to-be-computed set in the image after the stressing are specified for all pixels included within the range to-be-computed set in the image before the stressing, as a preparatory job for the arithmetic operation to be stated later. The correspondence process forms one of the characterizing features of the invention, and will be described with reference to FIGS. 9 and 10.

Figure 11:
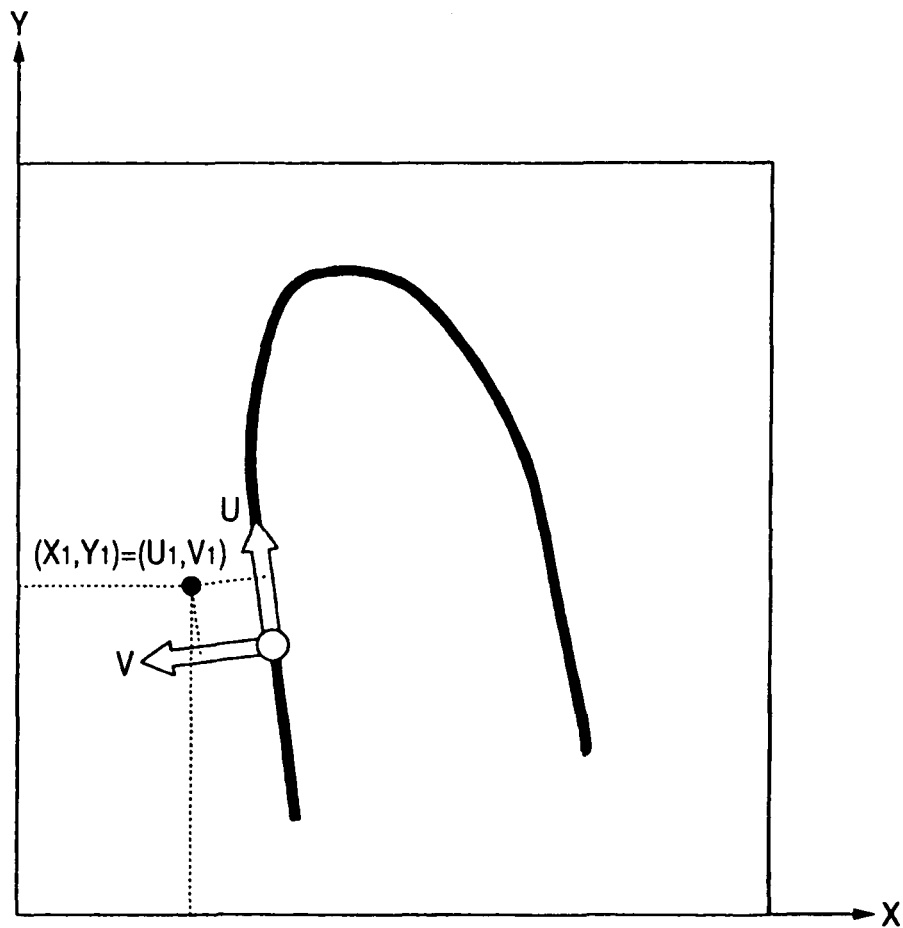
FIG. 11 is a diagram for explaining transformation from XY-coordinates on the image, into UV-coordinates on a ROI curve.

The arithmetic unit 26 first executes the processing of drawing out the respective ROIs set on both the images, into straight lines, under the control of the CPU 42 (step S11), whereupon it compares the full lengths of the ranges to-be-computed of both the images (step S12). Besides, the full lengths of both the ranges are equalized in such a way that, if the range to-be-computed of the image after the stressing is shorter as compared with that of the image before the stressing, the former is lengthened, and that, if the former is longer as compared with the latter, the former is shortened (step S13). Incidentally, regarding the processing of drawing out the ranges to-be-computed into the straight lines, as shown in FIG. 11, a position represented by XY-coordinates on the image may be geometrically coordinate-transformed onto a coordinate system where letter U denotes the tangential direction of the ROI curve, while letter V denotes the perpendicular direction thereof, so as to perform the processing on the UV-coordinate system. Then, it is facilitated to equalize the lengths of both the ROIs, or to bring the pixels of both the ROIs into correspondence.

(a) in FIG. 10 schematically illustrates the range to-be-computed before the stressing as is drawn out into the straight line (hereinbelow, termed "pre-stressing straight line"). The ROI is set on a u-axis, and the left end is the position of the starting point of the ROI setting, while the right end corresponds to the last point of the ROI setting. Besides, the range to-be-computed which extends the predetermined distance (for example, 5 mm) outside the set ROI is illustrated in the direction of a v-axis.

On the other hand, (b) in FIG. 10 schematically illustrates the range to-be-computed after the stressing as is drawn out into the straight line (hereinbelow, termed "post-stressing straight line"). In the stress echocardiography, the vasodilator drug is injected in order to stress the heart, so that a certain time period is required for an injecting operation and before the manifestation of the effect of the stressing. Consequently, the full lengths of the ROIs are sometimes different even when the same points are tracked, for the reason that the heart moves due to the motion of a patient or due to the shift of the probe attributed to the motion of the hand of the examiner. In this case, the numbers of pixels of both the ROIs are also different, and the pixels indicating an identical position cannot be brought into correspondence.

As shown at (c) in FIG. 10, therefore, the full length of the post-stressing straight line is increased or decreased so as to be equalized to that of the pre-stressing straight line (step S13). Thus, a point $(u_1, v_1)$ at the same position as that of a point $(u_0, v_0)$ on (a) in FIG. 10 is specified on (c) in FIG. 10. That is, all the pixels on (a) of FIG. 10 and all the pixels on (c) of FIG. 10 are brought into one-to-one correspondence (step S14).

Here, even when the lengthened or shortened post-stressing straight line is restored to its original length (step S15), the corresponding relationship can be held in such a way that pixels are interpolated or extrapolated by applying the idea of topology (step S16). In this case, the point $(u_1, v_1)$ on (c) in FIG. 10 becomes a point $(u_1', v_1)$ on (b) in FIG. 10. Incidentally, contrariwise to the above description, the pre-stressing straight line can, of course, be lengthened or shortened so as to equalize to the length of the post-stressing straight line.

Figure 12:
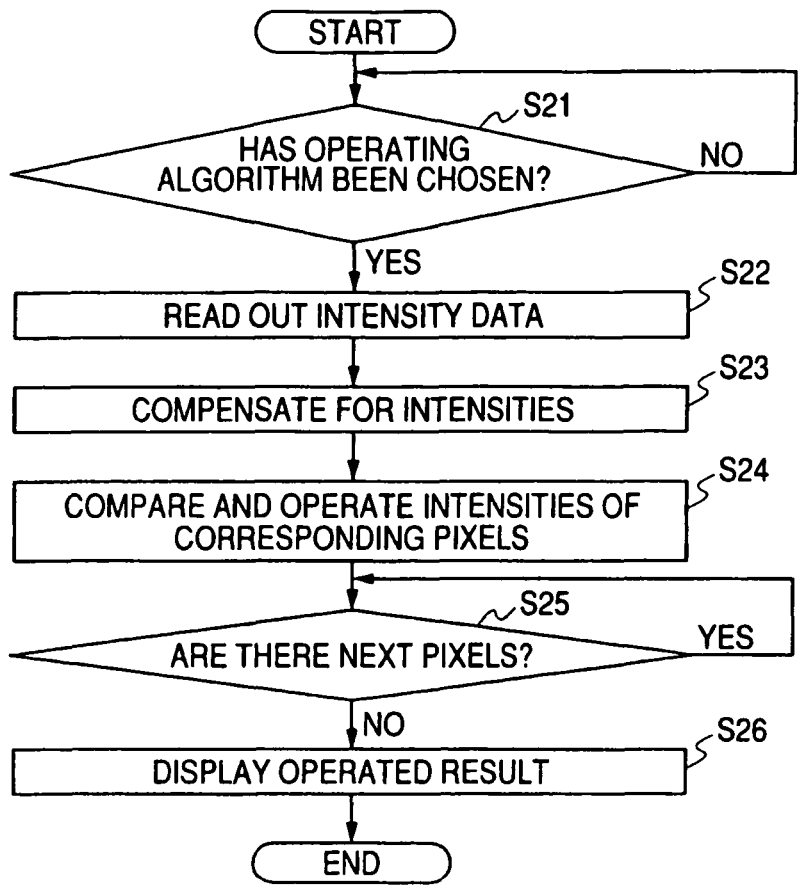
FIG. 12 is a flow chart showing the outline of a process for the operation between the image before the stressing and the image after the stressing.

When the preparatory job has been completed in this way, the CPU 42 commands the arithmetic unit 26 to execute the arithmetic operation process in which intensity data are compared between the images. The flow of the arithmetic operation process will be described with reference to FIG. 12.

The arithmetic unit 26 starts an arithmetic operation under the control of the CPU 42 when the operation start button 13D of the operation panel 13 has been pressed by the examiner. In this case, when only one operating algorithm exists, the arithmetic operation is started in such a way that the examiner merely presses the operation start button 13D. However, when a plurality of operating algorithms exist, the arithmetic operation is started in such a way that the examiner designates any of the operating algorithms (step S21).

Subsequently, the arithmetic unit 26 reads out the intensity data within the ranges to-be-computed of the respective images, from the image memory unit 17 (step S22).

Here, the CPU 42 commands the arithmetic unit 26 to execute the processing of compensating for the intensities of both the pre-stressing and post-stressing images (step S23). In the stress echocardiography, the injection of a contrast medium having been started is once ceased, and the vasodilator drug is injected instead. When a long time (for example, about 10 minutes) is expended on the injection of the vasodilator drug, the bubbles of the contrast medium will sometimes burst, thus lowering the density of the bubbles. Therefore, the contrast medium is injected anew. Herein, a situation might occur where the densities of the contrast medium will differ before and after the stressing, so the intensities cannot be directly compared. For this reason, the intensities are compensated for so that they may equalize at the brightest position of the heart cavity. Accordingly, in a case where such a problem does not occur, the compensation may well be omitted.

When the intensities have been compensated for, the pixels of both the ranges to-be-computed are arithmetically operated (step S24). The arithmetic operation may be subtraction or may well be division, and it is not limited to the technique of digital subtraction. Besides, although the arithmetic operation may be performed for the image intensity data (that is, the scattering intensities of ultrasounds) subjected to logarithmic compression processing, it may well be calculated while the following corrections are being made:

[Formula 1]

$$y = \exp(\alpha x) \quad (1)$$

Here, α: constant log(10)/10 ("log" denotes the natural logarithm), y: scattering intensity, and x: inverse transformation process which restores the logarithmic compression data by using the formula of the image intensity.

The arithmetic operation will be exemplified below.

[Formula 2]

$$power1 = a \cdot bubbleDensity1 = \int_0^T v_1(t)\,dt = V_1 T \quad (2)$$

$$power2 = a \cdot bubbleDensity2 = \int_0^T v_2(t)\,dt = V_2 T \quad (3)$$

$$\frac{power2}{power1} = \frac{V_2 T}{V_1 T} = \frac{V_2}{V_1} \quad (4)$$

Figure 13:
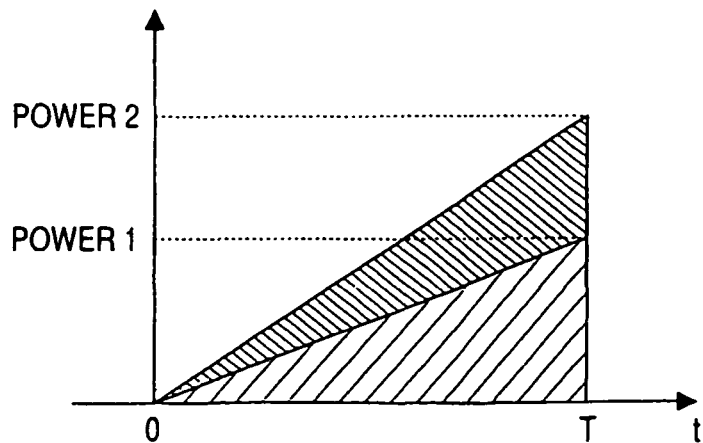
FIG. 13 is a graph for explaining the physical significance of an operated example according to the first embodiment.

Here, $\upsilon_1$ and $\upsilon_2$ denote bubble densities, $V_1$ and $V_2$ denote blood flow velocities, and T denotes a heart rate. Besides, letter a in Equations (2) and (3) denotes an acoustic factor such as decay, which differs depending upon places. As schematically shown in FIG. 13, the operated result is such that, at a normal part, the blood flow velocity $V_2$ after the stressing becomes higher than the blood flow velocity $V_1$ before the stressing, so $V_2/V_1$ becomes greater than one. That is, $V_2/V_1$ denotes an approximation to the quantity of blood (coronary reserve blood) which has increased in a case of expanding a coronary vein to the utmost under a certain blood pressure. In contrast, at a morbid part, the blood flow velocity $V_2$ after the stressing becomes lower than the blood flow velocity $V_1$ before the stressing, so that $V_2/V_1$ becomes less than one.

The arithmetic operation is iterated for all the corresponding pixels (step S25). When the arithmetic operations have ended, the operated results are delivered to the frame synthesis unit and are subjected to the image synthesis therein, whereupon the synthesized results are displayed on the monitor of the display unit 32 (step S26).

Figure 14:
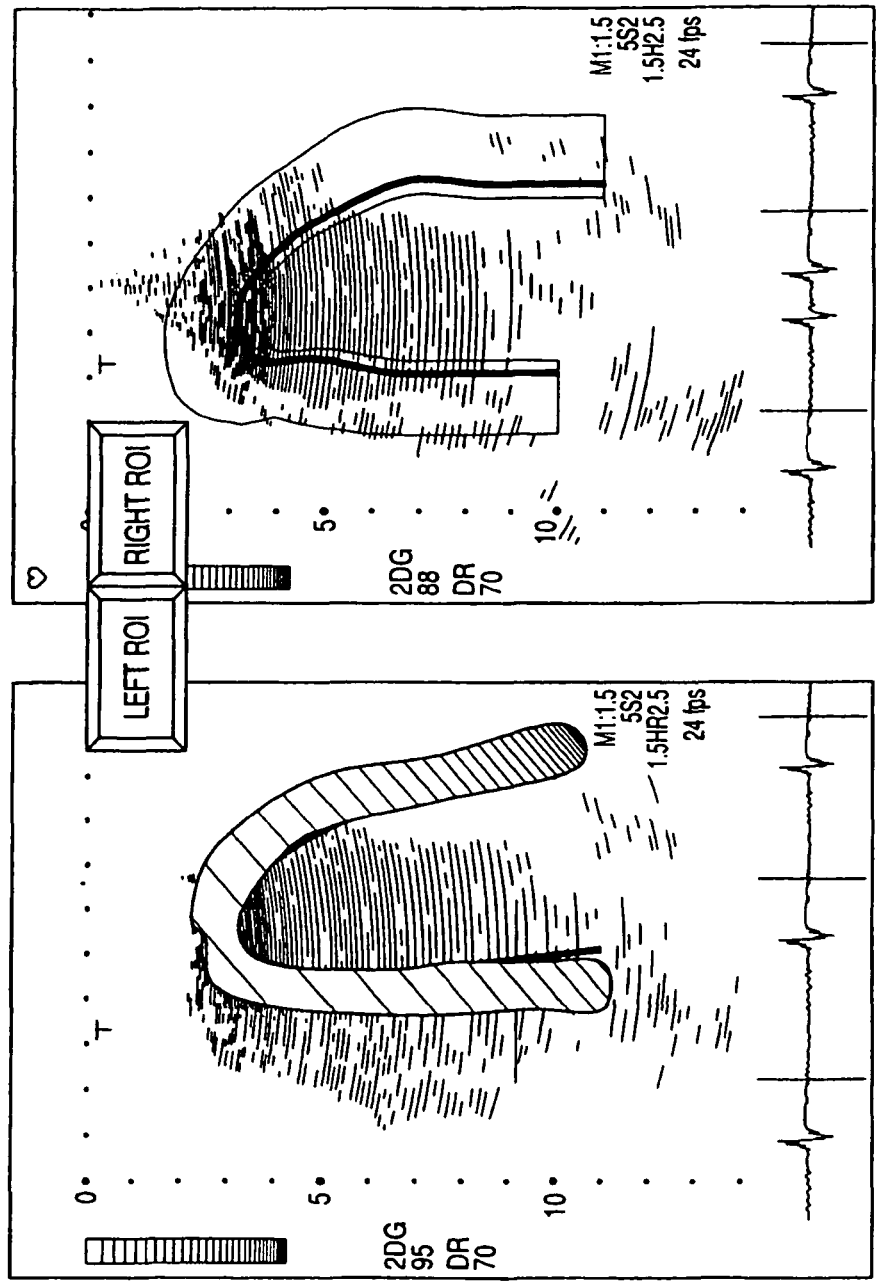
FIG. 14 is a diagram showing a display example of an operated result according to the first embodiment.

FIG. 14 shows a display example of the operated results. The operated results ($V_2/V_1$) of the individual points are displayed on the left image, namely, the image after the stressing. Color bars are rendered in a color expressive of lower velocities (for example, blue) for the operated results whose values are in the vicinity of one and less, whereas color bars are rendered in a color expressive of higher velocities (for example, red) as the values of the operated results become greater than one. Thus, the normal part and the morbid part can be clearly displayed in the separate colors, the morbid part is easily distinguished, and a diagnosability is enhanced. In this case, a color scale, the map of a maximum value, etc. can be set by the TCS 13E or the like in the operation panel 13.

Incidentally, the invention is not restricted to the construction of the foregoing embodiment, but it can be further performed in various aspects.

As a modification, a spatial filter may well be disposed in the B-mode DSC 24 so as to accept image signals into the spatial filter. Here, higher harmonic components are removed from spatial pixel value changes of the same depth for several adjacent rasters, thereby to perform spatial smoothing, and the image signals spatially smoothed are used for operations.

The spatial filter 7 is constructed of a digital filter of FIR type or IIR type, in which a coefficient string is convoluted into a pixel string to-be-filtered and in which the resulting pixel values are added up so as to be outputted. As is well known, the number of rasters for the spatial filtering and a cutoff frequency can be altered at will by freely changing the coefficient string.

Thus, image data with the influence of speckle noise relieved are generated.

Besides, although the above embodiment is constructed so as to execute the intensity compensation at the stage of the operation, it may well be constructed so as to execute the intensity compensation after displaying the image and before setting the ROI.

Subsequently, the second embodiment of the ultrasonic diagnostic equipment according to the invention will be described with reference to the accompanying drawings by similarly taking as an example the case where the blood flow velocity of a myocardial tissue is diagnosed.

Also the ultrasonic diagnostic equipment in this embodiment is identical or equivalent in construction to the ultrasonic diagnostic equipment according to the first embodiment as shown in FIG. 2, and its constituents shall be omitted from description by assigning the same reference numerals and signs thereto.

In this embodiment, unlike in the first embodiment, images after stressing are adopted as two images which are arithmetically operated.

Figure 15:
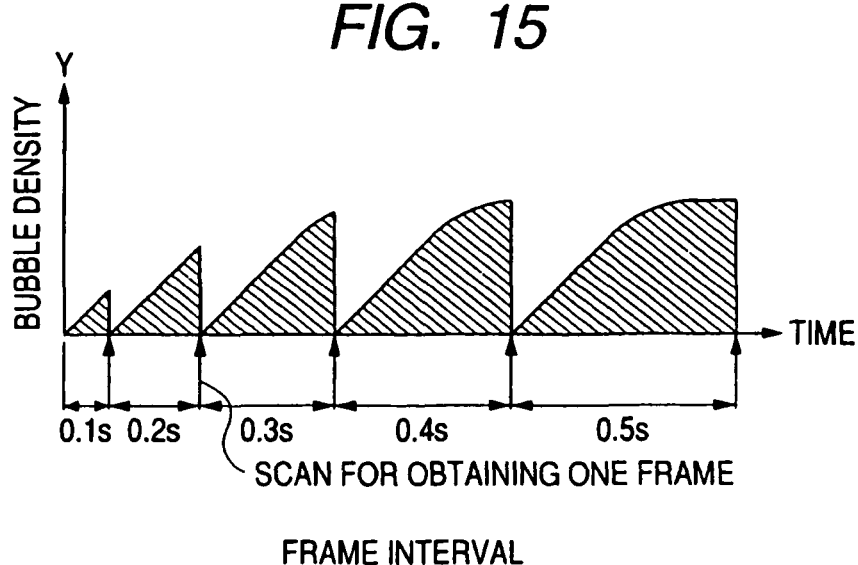
FIG. 15 is a graph for explaining the relationship between a frame interval and a bubble density.

In the case of the ultrasonic diagnostic equipment according to the first embodiment, a frame rate (the time interval of transmission) is controlled to be constant during observation. Of course, in a case where a depth or a scan line density has been altered, the frame rate changes, but the constant interval is usually held under fixed scan conditions. In contrast, in the case of the ultrasonic diagnostic equipment of this embodiment, the controller 31 changes the frame rate as shown in FIG. 15 by way of example, even under the fixed scan conditions. In the case of this example, the intermittent interval of a time period for obtaining the image data of one frame is preset by the run program of the CPU 42 so as to enlarge as "0.1 second, 0.2 second, 0.3 second, . . . and 1.0 second" with the lapse of time.

Incidentally, the frame interval may well be controlled so as to shorten with the lapse of time. Besides, in a case where an ultrasonic contrast medium is given by continuous intravenous drip infusion, a sequence shown in FIG. 15 may well be iterated.

Here will be elucidated fundamentals on which an image expressive of the extent of a blood stream is obtained by changing the frame interval. As shown in FIG. 15, after bubbles at an effective acoustic field traversing blood vessels have disappeared by ultrasound projection, the contrast medium (bubbles) immediately begins to flow into the acoustic field. In a case where the next ultrasound projection is effected in a comparatively short time, the quantity of bubbles which have flowed into the acoustic field is small. When the flash echo imaging method is performed in this bubble state, the intensity of an echo signal is relatively low because of the small quantity of bubbles. However, when the interval of the ultrasound projection is lengthened, the quantity of bubbles which flow in before projection increases as shown in the figure by way of example, and hence, the intensity of an echo signal heightens.

Therefore, letting a saturation time $T_{full}$ denote a time period in which an acoustic field effective for extinguishing bubbles by ultrasound projection (effective acoustic field) is filled up with the bubbles, the intensity of an echo signal to be obtained becomes constant even when the blood vessels are scanned at an interval longer than the saturation time $T_{full}$.

Figure 16:
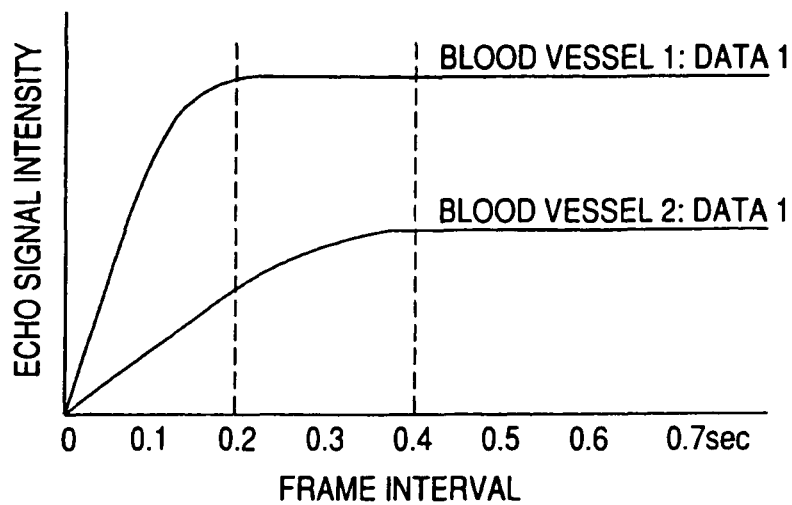
FIG. 16 is a graph for explaining the qualitative relationship between the frame interval and an echo signal intensity.

Such a relationship is exemplified in FIG. 16 by taking the frame interval on the axis of abscissas, and the echo signal intensity on the axis of ordinates. The figure shows a comparative example of two blood vessels 1 and 2 (data 1, data 2). The saturation time $T_{full}$ of the blood vessel 1 is 0.2 second, while the saturation time $T_{full}$ of the blood vessel 2 is 0.4 second. From this fact, it is understood that the blood-flow supply velocity of the blood vessel 1 is higher than that of the blood vessel 2, and that the signal intensity of the blood vessel 1 is higher, so the blood stream of the blood vessel 1 is larger.

On the basis of such fundamentals, the controller 31 changes the frame interval in accordance with the sequence of FIG. 15 by way of example. The image data of a plurality of frames obtained in accordance with the sequence are stored in the image memory 25. In this embodiment, arithmetic operations are executed on the basis of the image data thus obtained.

The operation of the CPU 42 after the entry thereof into the arithmetic operation mode is also the same as in the first embodiment except an arithmetic algorithm. Therefore, it will be explained here that, after a ROI has been set, the ROI is divided into several segments.

Figure 17:
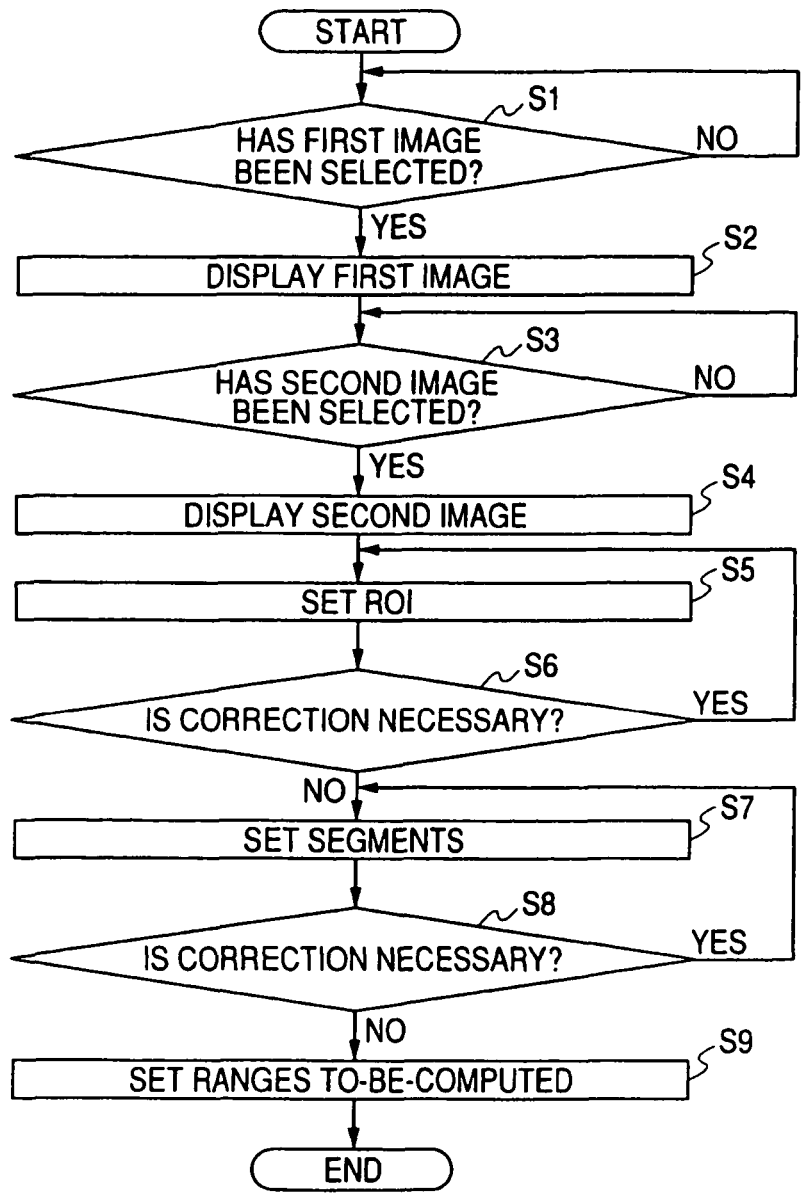
FIG. 17 is a flow chart showing the outline of a process for setting segments.

The flow of the segmentation is as shown in FIG. 17. Since steps down to the ROI setting completion (step S7) are the same as in the case of the first embodiment illustrated in FIG. 3, they shall be omitted from description by assigning the same reference signs thereto.

When the setting and correction of the ROI have been completed (step S6), the ROI is divided into several segments (step S7), and if necessary, any segment is corrected (step S8). Thereafter, each range to-be-computed is set as in the first embodiment (step S9).

As described in the first embodiment, the lengths of the ROIs sometimes become different each time an ultrasound is projected. The difference is ascribable, not only to a case where the cardiac wall lengthens or shortens as a whole, but also to a case where the cardiac wall lengthens at a part, but where it shortens at another part. Accordingly, the operation of bringing pixels into correspondence can be performed at a higher precision in the case of dividing the ROIs into the segments and comparing the lengths in terms of the respective segments, than in the case of comparing the lengths of the whole ROIs. When the display colors of the individual segments are changed, visual recognition is more facilitated.

Regarding the number of segments in this case, the region may well be divided into, for example, 6 segments or 5 segments in the case of a wall motion estimation as prescribed by learned societies such as the "ASE (American Society of Echocardiography). Alternatively, the region may well be merely equally divided without affording such a medical significance. The reason therefor is that, even with the equal division, the approximate position of a certain point is found more easily than in the case of viewing the whole ROI as the single straight line.

Figure 18:
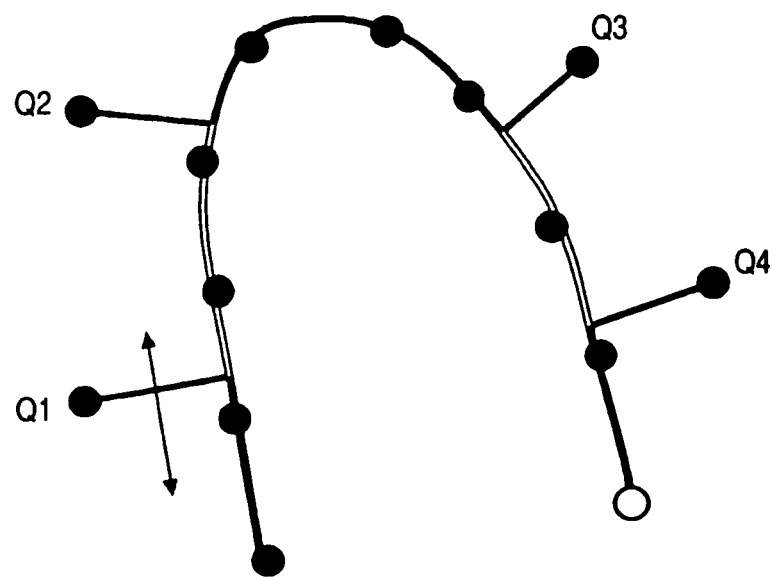
FIG. 18 is a diagram for explaining the setting and correction of the segments.

A method of setting the segments will be described with reference to FIG. 18. The operator first moves the track ball 13B or the like in the operation panel 13 to a feature point which is to form the boundary between divided segments, on an image displayed on the monitor of the display unit 29, and he/she presses the setting button, thereby to set a segment dividing point. Then, a line which extends perpendicularly to the ROI from the feature point is displayed, and a segment correcting point (Q1) is displayed on the extension. The segment correcting point is not displayed on the ROI for the reason that it is to be definitely distinguished from points which have been set at the ROI setting and which are left behind for ROI corrections. Thenceforth, segment dividing points Q2-Q4 are similarly set.

Any segment can be corrected by dragging the segment dividing point with the track ball or the like.

Thus, the segment dividing points are set at desired positions on the screen of the monitor of the display unit 29. Simultaneously, the positional information items of the segments are sent to the arithmetic unit 26.

By the way, in the case of the equally divided segments are set for each ROI, the segmentation can be automatically effected merely by designating the number of divisions. Besides, the setting of the segments can also be adopted in the case of the first embodiment.

As in the case of the first embodiment, the arithmetic operation in this embodiment may be subtraction or may well be division, and it is not limited to the technique of digital subtraction. Besides, although the arithmetic operation may be performed for the image intensity data (that is, the scattering intensities of ultrasounds) subjected to logarithmic compression processing, it may well be calculated while corrections based on inverse transformation are being made.

The arithmetic operation will be exemplified below.

[Formula 3] (5)

$$power1 = a \cdot bubbleDesity1 = \int_0^{T_1} v_1(t)dt = VT_1$$

-continued $$power2 = a \cdot bubbleDesity2 = \int_0^{T_2} v_2(t)dt = VT_2 \quad (6)$$

$$power2 - power1 = V(T_2 - T_1) \quad (7)$$

$$\frac{power2 - power1}{T_2 - T_1} = V(meanVelocity) \quad (8)$$

Figure 19:
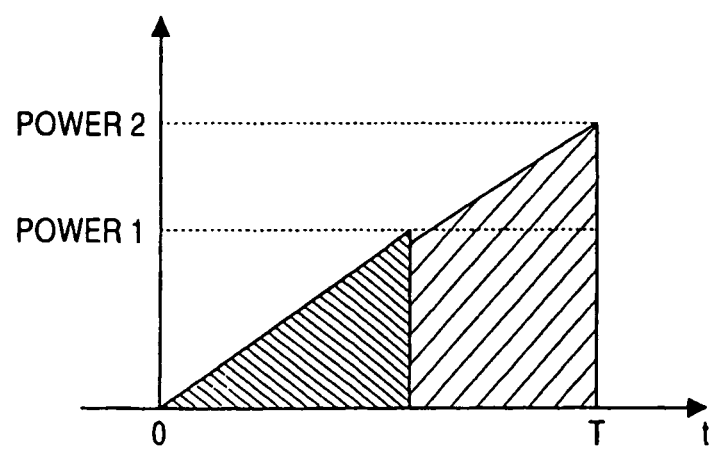
FIG. 19 is a graph for explaining the physical significance of an operated result according to the second embodiment.

Here, $v_1$ and $v_2$ denote bubble densities, V denotes a blood flow velocity, and $T_1$ and $T_2$ denote intermittent intervals. As schematically shown in FIG. 19, the operated result is such that, from the difference between an intensity obtained after the long intermittent interval and an intensity obtained after the short intermittent interval, the mean velocity V of a blood flow at a corresponding point can be computed. When such operated results are compared over the whole ROIs, a part of high blood flow velocity and a part of low blood flow velocity are clearly distinguished and displayed.

Figure 20:
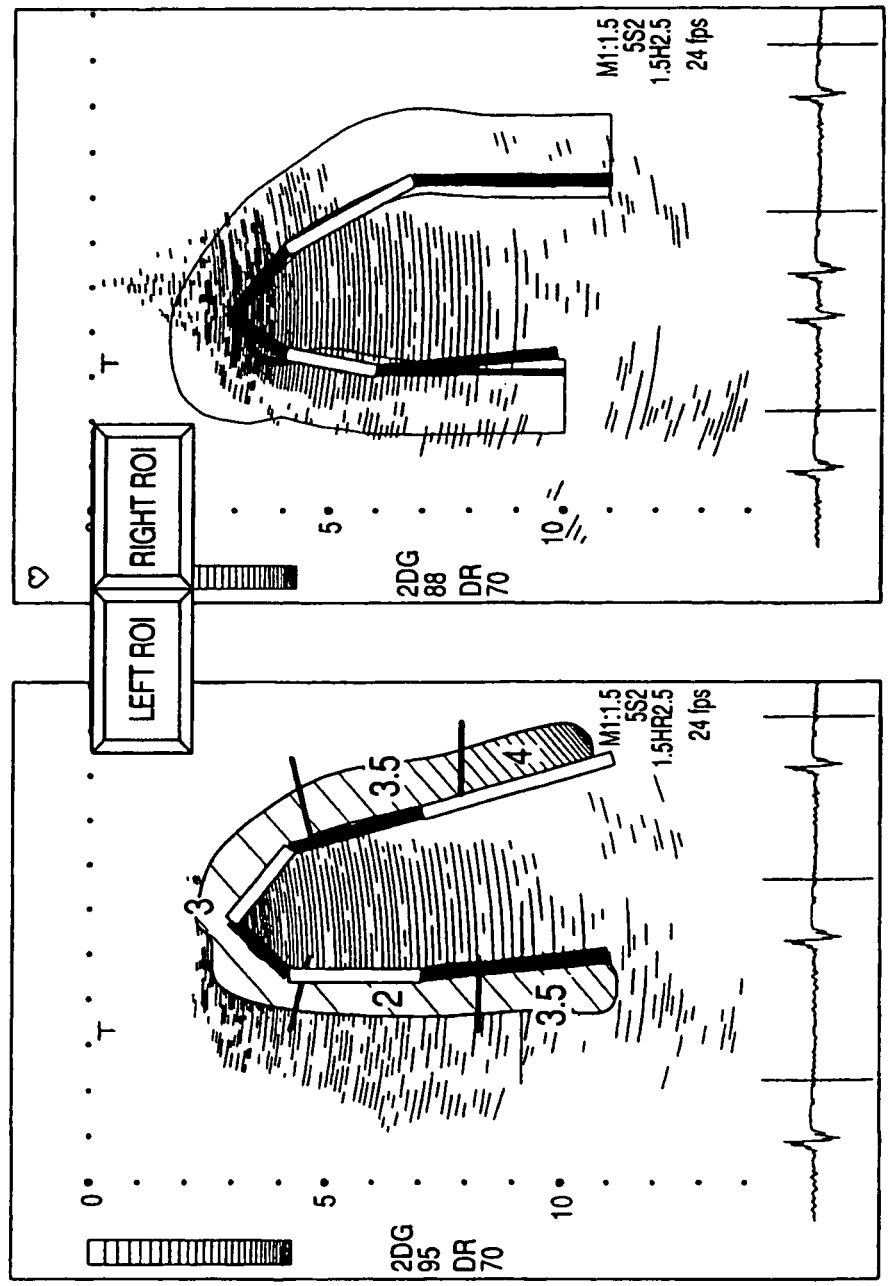
FIG. 20 is a diagram showing a display example of an operated result according to the second embodiment.

FIG. 20 shows a display example of the operated results. The mean velocities V being the operated results of the individual points are displayed on the left image. Color bars are rendered in a color expressive of lower velocities (for example, blue) for the operated results whose values are in the vicinity of a preset value and less, whereas color bars are rendered in a color expressive of higher velocities (for example, red) as the values of the operated results become greater than the vicinity of the preset value. Thus, a normal part and a morbid part can be clearly displayed in the separate colors, the morbid part is easily distinguished, and a diagnosability is enhanced. In this case, a color scale, the map of a maximum value, etc. can be set by the TCS 13E or the like in the operation panel 13.

Subsequently, a modification to the second embodiment will be described. Whereas the second embodiment concerns the general case, the modified embodiment executes either of the two times of ultrasound projection after the blood vessels have been saturated with the contrast medium, in other words, it executes the computation by employing intensities in the case where the time interval of the ultrasound projection has been lengthened to a certain degree.

Figure 21:
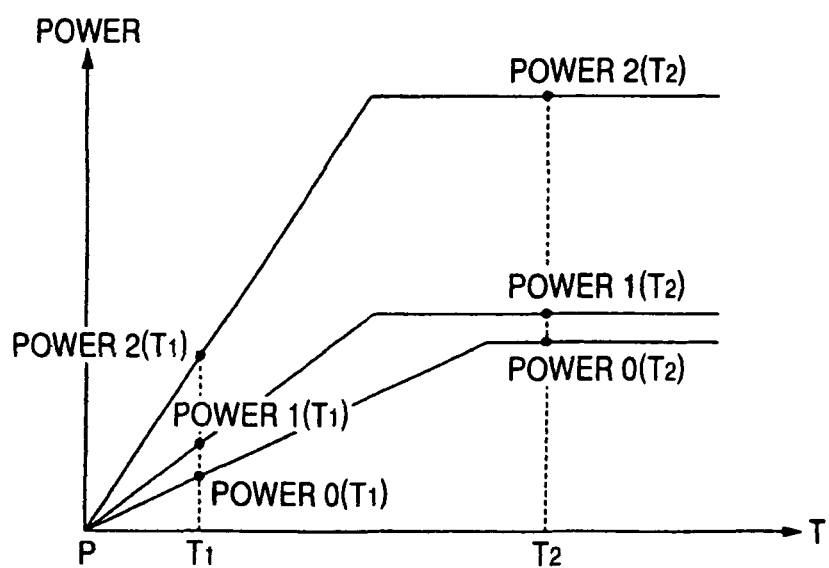
FIG. 21 is a graph for explaining the physical significance of an operated example according to a modification to the second embodiment.

FIG. 21 is a diagram showing the relationship between the power of a blood flow and the time in the modified embodiment. It illustrates the blood flow powers "power1" and "power2" of two normal parts and the blood power "power0" of a morbid part.

At the morbid part, a blood flow velocity is not great, and hence, the corresponding blood flow power is not high after the lapse of a comparatively short time period ($T_1$) since the last ultrasound projection (Power0 ($T_1$) in the figure). On the other hand, even at the normal part, there is a part at which the blood flow power after the lapse of the time period $T_1$ is not high (Power1 ($T_1$) in the figure). This is ascribable to, for example, the fact that a reflected wave has decayed due to the existence of a rib, the lung or the like. With only the measurement after the time period $T_1$, accordingly, it is difficult to judge whether the pertinent part is the normal part or the morbid part.

Moreover, even in a measurement after a comparatively long time period ($T_2$) since the last ultrasound projection, that is, after the blood vessels have been saturated with the contrast medium, a part which exhibits a blood flow power as low as in the morbid part exists in spite of the normal part, and the relationship does not differ from that in the measurement after the lapse of the time period $T_1$. Anyway, the detection of the morbid part is difficult with only one time of measurement.

Therefore, the relationship between the blood flow power after the lapse of the time period $T_1$ and the blood flow power after the lapse of the time period $T_2$ is investigated. By way of example, when the ratio of both the powers is evaluated, the following relationship holds:

[Formula 4] (9)
$$\frac{\text{power}(T_1)}{\text{power}(T_2)} = \frac{a \cdot V \cdot T_1 \cdot bubbleDensity}{a \cdot V \cdot T_2 \cdot bubbleDensity} = \frac{a \cdot V \cdot T_1 \cdot bubbleDensity}{a \cdot A \cdot bubbleDensity} = \frac{V \cdot T_1}{A}$$

Here, letter A denotes the intensity after the blood vessels have been saturated with the contrast medium. The intensity is proportional to the blood flow velocity in the pertinent place, and it is constant in that place as long as the blood vessels are saturated with the contrast medium. Accordingly, the acoustic factor a, such as decay, which differs depending upon places, and the bubble density are erased from the relational equation, and the ratio of the blood flow velocity of each myocardial part after the identical elapsed time T can be found.

Referring back to FIG. 21, merely the blood flow power "power1($T_1$)" of the normal part appears to be lower than "Power2($T_1$)" on account of the intervention of the rib, the lung or the like, and hence, the ratios $V \cdot T_1/A$ of both the powers are equal, whereas the ratio $V \cdot T_1/A$ of the morbid part is small, and the following relationship holds:

[Formula 5] (10)
$$\frac{\text{power}(T_1)}{\text{power}(T_2)} = \frac{power2(T_1)}{power2(T_2)} > \frac{power0(T_2)}{power0(T_2)}$$

Figure 1A:
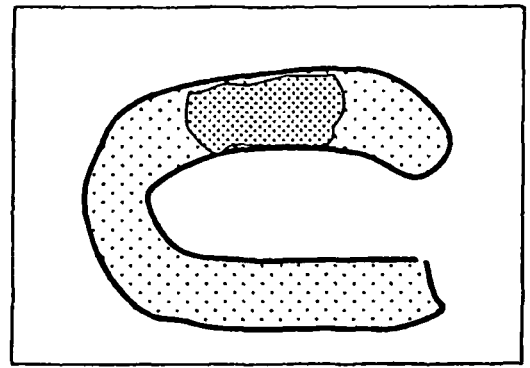
Figure 1B:
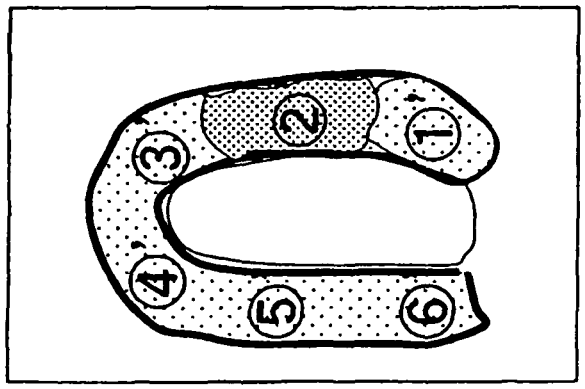
Figure 1C:
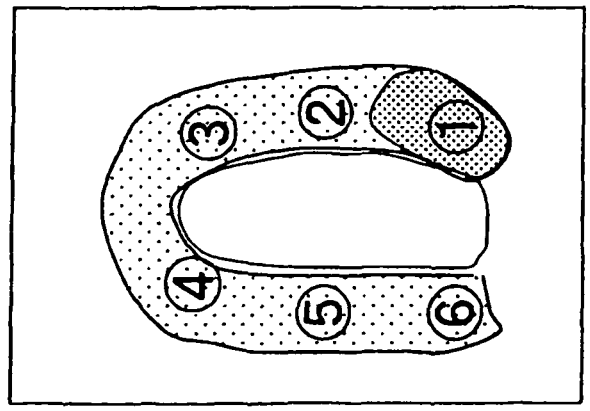

Thus, the fundamental principle of the invention as described with reference to FIG. 1 holds true also in the modified embodiment. Herein, an image at the time $T_1$ in this modified embodiment corresponds to the image "before stressing" in FIG. 1A, and an image at the time $T_2$ in this modified embodiment corresponds to the image "after the stressing" in FIG. 1B. As the result of the arithmetic operation between both the images, the distinction between the normal part and the morbid part is definitely displayed on an image in the same manner as shown in FIG. 1C.

Besides, when an arithmetic operation in which the ratio $V \cdot T_1/A$ evaluated by the arithmetic operation based on the modified embodiment is further divided by $T_1$, V/A is found, and it is permitted to obtain an image which directly displays normalized myocardial blood supply velocities.

Various modifications can be further made to these embodiments. By way of example, operated results can be displayed, not only as an image, but also as numerical values. More specifically, when a cursor is located at an operated result area on the monitor of the display unit 29, the operated result of the pertinent part can be displayed.

Moreover, although the embodiments have been described as to the arithmetic operations executed for the intensity data of the images, the arithmetic operations may be executed with any of RF data, IQ data, raw data, etc.

Besides, although the embodiments have been described as to the two-dimensional images, the invention can also be applied to three-dimensional images. Further, arithmetic operations can be executed with three or more images.

Incidentally, although the foregoing embodiments have been described in the aspect of the ultrasonic diagnostic equipment, various modifications are possible in this regard. The equipment of the invention may be unitarily incorporated in another modality, and it may well be performed as a dedicated apparatus for re-processing image data acquired once, for example, a workstation. It is also allowed to handle image data which are acquired by any technique other than the flash echo imaging of the ultrasonic diagnostic equipment.

Furthermore, the above embodiments are merely for the purpose of description, and they shall not limit the scope of the invention. Accordingly, one skilled in the art can adopt aspects of performance in which the individual constituents or all the constituents are substituted by equivalents to them, and such aspects of performance shall be also covered within the scope of the invention.

What is claimed is:

1. An ultrasonic diagnostic equipment, comprising:
   a memory configured to store a first contrast image generated by scanning an object with ultrasonic beams before stressing the object, and a second contrast image generated by scanning the object with ultrasonic beams after the stressing; and
   an arithmetic circuit configured to operationally connect to the image memory and to calculate an index value indicating an effect caused by the stressing, by using intensities of the first and second contrast images.

2. The ultrasonic diagnostic equipment as defined in claim 1, wherein the arithmetic circuit is configured to transform ultrasonic signals acquired by the scannings onto a linear scale, the ultrasonic signals being subjected to logarithmic compression.

3. The ultrasonic diagnostic equipment as defined in claim 1, wherein the arithmetic circuit is configured to calculate coronary reserve blood on a basis of the first contrast image generated by scanning the object with ultrasonic waves before the stressing and the second contrast image generated by scanning the object with ultrasonic waves after the stressing.

4. The ultrasonic diagnostic equipment as defined in claim 1, wherein the arithmetic circuit is configured to calculate an average of blood supply velocities between the first and second contrast images each generated by scanning the object with ultrasonic waves after the stressing, the first and second contrast images being of different intermittent intervals.

5. The ultrasonic diagnostic equipment according to claim 1, wherein the arithmetic circuit is configured to calculate the index value by using intensities of a first position in the first contrast image and a second position in the second image, the first and second positions being a substantially same position.

6. The ultrasonic diagnostic equipment as defined in claim 5, wherein the arithmetic circuit is configured to compare the intensities of a same position of a heart cavity part of the two contrast images and to compensate for the intensities of the same position.

7. The ultrasonic diagnostic equipment according to claim 5, wherein the arithmetic circuit is configured to calculate the index value by dividing the intensity of the second position by the intensity of the first position.

8. The ultrasonic diagnostic equipment as defined in claim 7, further comprising:
   a display configured to display a divisional image made by the dividing, the first and second positions indicating a portion contained in a segmented ROI set for a myocardium.

9. The ultrasonic diagnostic equipment as defined in claim 8, wherein each of the segmented ROIs of the first and second contrast images includes three segments, which are a base part, a middle part, and an apex part of the myocardium.

10. The ultrasonic diagnostic equipment as defined in claim 8, wherein each of the segmented ROIs of the first and second contrast images includes five segments, which are a left base part, a left middle part, an apex part, a right middle part, and a right base part of the myocardium.

11. The ultrasonic diagnostic equipment as defined in claim 8, wherein the display is further configured to display the first and second contrast images in parallel.

12. The ultrasonic diagnostic equipment as defined in claim 8, wherein the display is configured to display the divisional image in colors in accordance with divisional values.

13. The ultrasonic diagnostic equipment as defined in claim 8, wherein the arithmetic circuit is configured to
set a first curved ROI on the first contrast image and a second curved ROI on the second contrast image, wherein a portion of a boundary of the first and second curved ROIs is curved and each of the first and second curved ROIs being defined by first and second sets of points, respectively, in a first coordinate system, the first and second curved ROIs being the segmented ROI; and
position the points of the first contrast image and the corresponding points thereof of the second contrast image on a basis of the first and second curved ROIs.

14. The ultrasonic diagnostic equipment as defined in claim 13, wherein the arithmetic circuit is configured to set the curved ROIs by automatically subjecting a plurality of previously chosen points to curve fittings.

15. The ultrasonic diagnostic equipment as defined in claim 14, wherein the arithmetic circuit is configured to reset the curved ROIs in such a way that, when the plurality of chosen points are moved by an operator, the curves delineated by curve fittings are automatically moved in accordance with movement of the chosen points.

16. The ultrasonic diagnostic equipment as defined in claim 13, wherein the arithmetic circuit is configured to
coordinate-transform the first and second sets of points in the first curved ROI and the second curved ROI, respectively, to generate a first rectangular ROI and a second rectangular ROI by coordinate-transforming the first and second sets of points to corresponding sets of points in the second coordinate system;
execute a processing of at least one of elongating and contracting a length of a side of at least one of the first rectangular ROI and the second rectangular ROI in the second coordinate system to generate first and second matched ROIs in the second coordinate system in which a whole length of the side of the first matched ROI and a whole length of the side of the second matched ROI are matched with each other; and
coordinate-transform each point in the first and second matched ROIs to corresponding points in the first coordinate system to generate first and second restored ROIs.

17. The ultrasonic diagnostic equipment according to claim 5, wherein the intensity of the first position is a brightness value at a pixel indicated by the first position, and the intensity of the second position is a brightness value at a pixel indicated by the second position.

18. The ultrasonic diagnostic equipment according to claim 5, wherein the first position is a region consisting of a plurality of pixels in the first contrast image, and the second position is a region consisting of a plurality of pixels in the second contrast image.

19. The ultrasonic diagnostic equipment according to claim 5, wherein the arithmetic circuit is configured to calculate the index value by subtracting the intensity of the first position from the intensity of the second position.

20. The ultrasonic diagnostic equipment according to claim 1, wherein the first contrast image is generated by scanning the object with ultrasonic waves after a prior injection of a contrast medium and before the stressing, and the second contrast image generated by scanning the object with ultrasonic waves after a posterior injection of the contrast medium and after the stressing.

21. The ultrasonic diagnostic equipment as defined in claim 20, wherein the arithmetic circuit is configured to generate the second contrast image so as to illustrate a steal phenomenon.

22. The ultrasonic diagnostic equipment according to claim 20, wherein the stressing is an injection of a vasodilator drug.

23. The ultrasonic diagnostic equipment according to claim 5, wherein the first and second positions indicate a portion of a myocardium.

24. The ultrasonic diagnostic equipment according to claim 23, wherein the portion is contained in a segmented region of interest (ROI) set for the myocardium.

25. An image processing apparatus, comprising:
an image memory configured to store a first contrast image of an object before stressing for the object, and a second contrast image of the object after the stressing; and
an arithmetic circuit configured to operationally connect to the image memory and to calculate an index value indicating an effect caused by the stressing, by using intensities of the first and second contrast images.

26. The image processing apparatus according to claim 25, wherein the arithmetic circuit is configured to calculate the index value by using intensities of a first position in the first contrast image and a second position in the second image, the first and second positions being a substantially same position.

27. The image processing apparatus according to claim 26, wherein the arithmetic circuit is configured to calculate the index value by dividing the intensity of the second position by the intensity of the first position.

28. The image processing apparatus according to claim 26, wherein the intensity of the first position is a brightness value at a pixel indicated by the first position, and the intensity of the second position is a brightness value at a pixel indicated by the second position.

29. The image processing apparatus according to claim 26, wherein the first position is a region consisting of a plurality of pixels in the first contrast image, and the second position is a region consisting of a plurality of pixels in the second contrast image.

30. The image processing apparatus according to claim 26, wherein the arithmetic circuit is configured to calculate the index value by subtracting the intensity of the first position from the intensity of the second position.

31. The image processing apparatus according to claim 25, wherein the first contrast image is generated after a prior injection of a contrast medium and before the stressing, and the second contrast image generated after a posterior injection of the contrast medium and after the stressing.

32. The image processing apparatus according to claim 31, wherein the stressing is an injection of a vasodilator drug.

33. The image processing apparatus according to claim 26, wherein the first and second positions indicate a portion of a myocardium.

34. The image processing apparatus according to claim 33, wherein the portion is contained in a segmented region of interest (ROI) set for the myocardium.

35. The image processing apparatus according to claim 25, wherein the image memory is configured to store the first contrast image, which is generated by scanning the object with ultrasonic waves before stressing for the object, and the second contrast image, which is generated by scanning the object with ultrasonic waves after the stressing.

36. An ultrasonic diagnostic method, comprising:
generating a first contrast image by scanning an object with ultrasonic waves before stressing the object and a second contrast image by scanning the object with ultrasonic waves after the stressing, the object including a contrast medium; and
calculating an index value indicating an effect caused by the stressing, by using intensities of the first and second contrast images.

* * * * *